(12) United States Patent
Skulachev et al.

(10) Patent No.: US 9,744,180 B2
(45) Date of Patent: Aug. 29, 2017

(54) PHARMACEUTICAL FORMULATIONS CONTAINING MITOCHONDRIALLY TARGETED ANTIOXIDANTS

(71) Applicant: Mitotech SA, Luxembourg (LU)

(72) Inventors: Maxim V Skulachev, Moscow (RU); Vladimir P. Skulachev, Moscow (RU); Egor Y Plotnikov, Noginsky (RU); Dmitry B Zorov, Moscow (RU); Roman A Zinovkin, Moscow (RU); Alexander N Lukashev, Moscow (RU); Maxim V Egorov, Moscow (RU); Maxim L Lovat, Moscow (RU); Anton Petrov, Woodland Hills, CA (US)

(73) Assignee: MITOTECH SA, Luxembourg (LU)

( * ) Notice: Subject to any disclaimer, the term of this patent is extended or adjusted under 35 U.S.C. 154(b) by 0 days.

(21) Appl. No.: 14/803,789

(22) PCT Filed: Jan. 21, 2014

(86) PCT No.: PCT/US2014/012353
§ 371 (c)(1),
(2) Date: Jul. 20, 2015

(87) PCT Pub. No.: WO2014/116591
PCT Pub. Date: Jul. 31, 2014

(65) Prior Publication Data
US 2016/0243136 A1    Aug. 25, 2016

Related U.S. Application Data

(60) Provisional application No. 61/755,234, filed on Jan. 22, 2013.

(51) Int. Cl.
*A61K 31/662*    (2006.01)
*A61K 31/352*    (2006.01)
*A61K 31/4375*   (2006.01)
*A61K 31/4745*   (2006.01)

(52) U.S. Cl.
CPC .......... *A61K 31/662* (2013.01); *A61K 31/352* (2013.01); *A61K 31/4375* (2013.01); *A61K 31/4745* (2013.01)

(58) Field of Classification Search
None
See application file for complete search history.

(56) References Cited

PUBLICATIONS

Hawley's Condensed Chemical Dictionary, 15th edition, Lewis, R., ed., at p. 711.*
Silva, T. Mini Rev Med Chem 2005 vol. 5 pp. 893-914.*

* cited by examiner

*Primary Examiner* — Heidi Reese
(74) *Attorney, Agent, or Firm* — Wayne A Keown; Verrill Dana, LLP

(57) ABSTRACT

The present disclosure provides methods of preventing activation of neutrophils with mitochondrially targeted antioxidants. Also disclosed are methods of preventing or treating different inflammatory diseases and inflammation-related conditions with MTAs.

8 Claims, 15 Drawing Sheets

Control

Pyelonephritis

Pyelonephritis
+ SkQR1

Control

Pyelonephritis

Pyelonephritis
+ SkQR1

Control

Pyelonephritis

Pyelonephritis
+ SkQR1

Control RTC

RTC+LC+BL

Fig. 9A        Fig. 9B        Fig. 9C        Fig. 9D
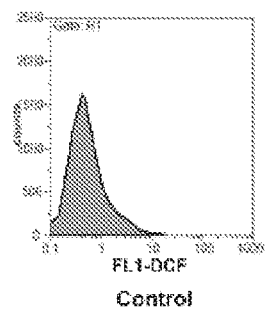 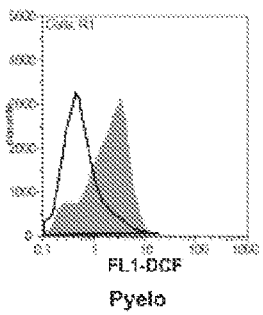 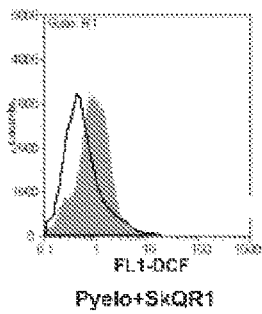 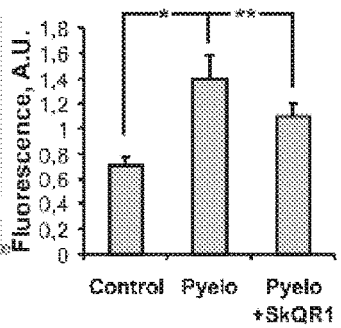
Fig. 10A                    Fig. 10B
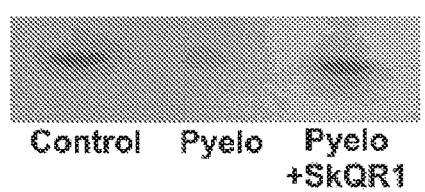        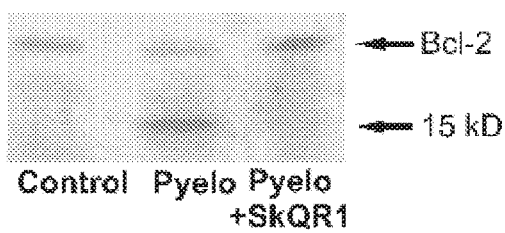
Fig. 10C                    Fig. 10D
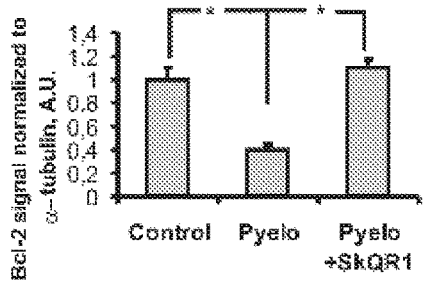        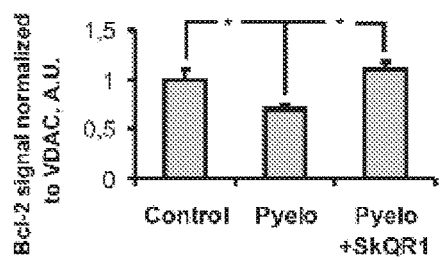

Fig 15A    Fig. 15B
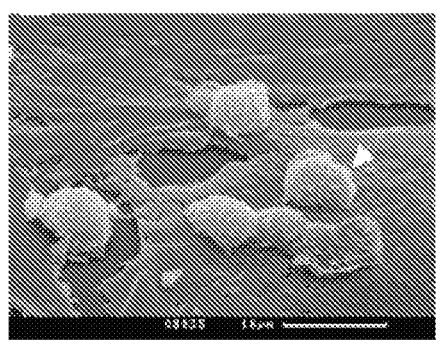 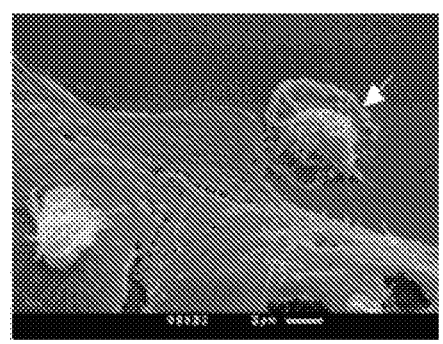
Fig. 16
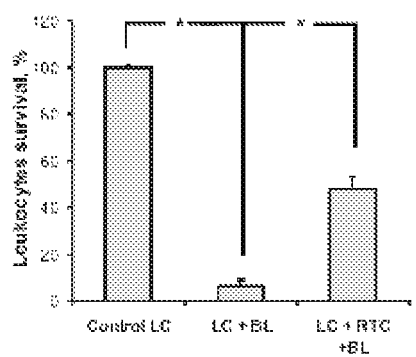

PHARMACEUTICAL FORMULATIONS CONTAINING MITOCHONDRIALLY TARGETED ANTIOXIDANTS

CROSS REFERENCE TO RELATED APPLICATIONS

This application claims priority to and the benefit of U.S. Provisional Patent Application No. 61/755,234, entitled "Method of Treatment of Inflammatory Conditions With Mitochondrially Targeted Antioxidants," filed on Jan. 22, 2013, the entire contents of which are incorporated by reference herein.

FIELD OF THE INVENTION

This disclosure is in the fields of pharmacology and medicine, and in particular, to inflammation and related conditions.

BACKGROUND

Leukocyte infiltration in response to bacterial invasion can be a contributor to tissue damage (Gupta et al. (1996b) *Kidney Int.* 49:26-33). Leukocyte infiltration in response to pathogen infection does not result in pathological changes in the tissue as long as reactive oxygen species (ROS) formed by leukocytes and macrophages stay within the phagocytic vacuoles inside of these cells. However, the general mechanism of anti-pathogen response (in the case of infection-induced inflammation) involves generation of ROS by neutrophil and macrophage NADPH oxidases (Sanmun et al. (2009) *Am. J. Physiol. Cell. Physiol.* 297:C621-631). The extracellular release of ROS becomes damaging and leads to tissue injury and dysfunction (Mundi et al. (1991) *Infect. Immun,* 59:4168-4172). In addition to ROS release, the inflammatory response also involves release of cytokines, eicosanoids, complement activation and mobilization of destructive enzymes (Nassar and Badr (1998) *J. Nephrol.* 11:177-184), and mononuclear cells (MNCs) i.e., macrophages and monocytes, play a role in such tissue damage (Friedewald and Rabb (2004) *Kidney Int.* 66:486-491). For example, it has been demonstrated that fibrosis, a hallmark of tissue damage, is much less pronounced when the level of monocyte infiltration in the kidney is low.

Acute Pyelonephritis (APN) is an example of a disorder initially caused by a bacterial infection and in which the inflammatory response to the infection leads to kidney injury and dysfunction. Although the kidney and urinary tract are normally germ-free, during their lifetime, about 40% of women and 12% of men experience urinary tract infections (UTIs) (O'Hanley, (1996) In: *Urinary Tract Infections: Molecular Pathogenesis and Clinical Management* (Mobley et al., eds), (Washington, D.C.: ASM Press), pp. 405-425). APN is a potentially life-threatening complication of UTI which occurs when infection progresses to the upper urinary tract. The uropathogen most frequently associated with this disease is the pyelonephritogenic subset of *Escherichia* coli, which is implicated in up to 85% of both complicated and uncomplicated UTIs (Hill et al. (2005) *Obstet. Gynecol.* 105:18-23).

Pharmacological treatment of APN is used to manage the oxidative stress response, thereby providing a therapeutic effect in preventing renal pathologies (Aydogdu et al. (2006) *Gin. Exp. Pharmacol. Physiol.* 33:119-124; Koyner et al. (2008) *Nephron. Exp. Nephrol.* 109:e109-117; Polo-Romero et al. (2004) *Ren. Fail.* 26:613-618; Rodrigo et al. (2004) *Nephrol. Dial. Transplant.* 19:2237-2244; Sadeghi et al. (2008) *Pediatr. Nephrol.* 23:1503-1510; Singh et al. (2004) *Toxicology* 201:143-151). However, treatment is complicated by the diversity of ROS generating mechanisms, and their differential contribution to host defense from infection and collateral tissue damage. Mitochondria and NADPH oxidases are the two principle sources of ROS, although their relative contribution to inflammatory pathologies is not well defined.

Thus, what is needed are improved methods of treating, or inhibiting, or preventing the ROS-release-related tissue damage resulting from inflammation accompanying certain disorders.

SUMMARY

It has been determined that key elements of certain inflammatory disorders are excessive mitochondrial reactive oxygen species (ROS) generated in all steps of the pathological progression. This discovery has been exploited to provide the present methods of alleviating or reducing oxidative stress in certain tissues by targeting MTAs to mitochondria in those tissues. It has also been discovered that MTAs prevent activation of neutrophils during the inflammatory process, thereby reducing the damaging effects of inflammation in disorders.

Accordingly, in one aspect, the disclosure provides a method of preventing neutrophil activation, comprising contacting a sample containing neutrophils with a mitochondrially targeted antioxidant having the structure:

wherein:
A is an effector moiety having a following structure:

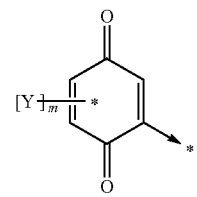

and/or reduced forms thereof, wherein:
m is an integer from 1 to 3;
each Y is independently selected from the group consisting of:
lower alkyl;
lower alkoxy; or
two adjacent Y groups, together with carbon atoms to which they are attached, form a following structure:

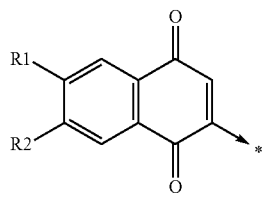

and/or reduced forms thereof; wherein:
R1 and R2 may be the same or different and are each independently lower alkyl or lower alkoxy;
L is a linker group, comprising:
a) a straight or branched hydrocarbon chain which can be optionally substituted by one or more substituents and optionally contains one or more double or triple bonds; or
b) a natural isoprene chain;
n is integer from 1 to 40, or from 2 to 15, or from 5 to 11;
B is a targeting group comprising Sk$^+$Z$^-$, wherein:
Sk is a lipophilic cation; and
Z is a pharmacologically-acceptable anion,
and solvates, salts, isomers or prodrugs thereof.

In some embodiments, the MTA is SkQ1, SkQ1H$_2$, SkQR1, SkQR1H$_2$, SkQ3, SkQ3H$_2$, SkQRB, SkQRBH$_2$, SkQB1, SkQB1H$_2$, SkQBP1, and/or SkQBP1H$_2$. In one embodiment, the sample is a blood sample.

In another aspect, the present disclosure provides a method of preventing MMP-9 release from activated neutrophils, comprising contacting the activated neutrophils with a mitochondrially targeted antioxidant having the structure:

wherein:
A is an effector moiety having a following structure:

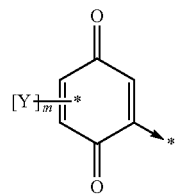

and/or reduced forms thereof, wherein:
m is an integer from 1 to 3;
each Y is independently selected from the group consisting of:
lower alkyl;
lower alkoxy; or
two adjacent Y groups, together with carbon atoms to which they are attached, form a following structure:

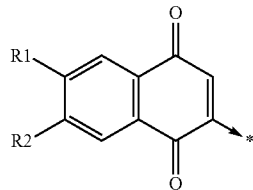

and/or reduced forms thereof; wherein:
R1 and R2 may be the same or different and are each independently lower alkyl or lower alkoxy;
L is a linker group, comprising:
a) a straight or branched hydrocarbon chain which can be optionally substituted by one or more substituents and optionally contains one or more double or triple bonds; or
b) a natural isoprene chain;
n is integer from 1 to 40, or from 2 to 15, or from 5 to 11;
B is a targeting group comprising Sk$^+$Z$^-$, wherein:
Sk is a lipophilic cation; and
Z is a pharmacologically-acceptable anion,
and solvates, salts, isomers or prodrugs thereof.

In some embodiments, the antioxidant is SkQ1, SkQ1H$_2$, SkQR1, SkQR1H$_2$, SkQ3, SkQ3H$_2$, SkQRB, SkQRBH$_2$, SkQB1, SkQB1H$_2$, SkQBP1, and/or SkQBP1H$_2$.

In another aspect, the disclosure provides a method of treating a patient suffering from an inflammatory disorder, comprising: administering to the patient a therapeutically effective amount of a mitochondrially targeted antioxidant having the structure:

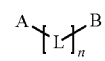

wherein:
A is an effector moiety having a following structure:

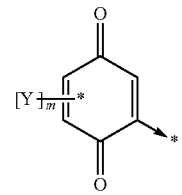

and/or reduced forms thereof, wherein:
m is an integer from 1 to 3;
each Y is independently selected from the group consisting of:
lower alkyl;
lower alkoxy; or
two adjacent Y groups, together with carbon atoms to which they are attached, form a following structure:

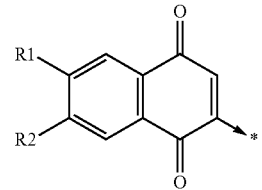

and/or reduced forms thereof; wherein:
R1 and R2 may be the same or different and are each independently lower alkyl or lower alkoxy;
L is a linker group, comprising:
a) a straight or branched hydrocarbon chain which can be optionally substituted by one or more substituents and optionally contains one or more double or triple bonds; or
b) a natural isoprene chain;
n is integer from 1 to 40, or from 2 to 15, or from 5 to 11;
B is a targeting group comprising Sk$^+$Z$^-$, wherein:
Sk is a lipophilic cation; and
Z is a pharmacologically-acceptable anion,
and solvates, salts, isomers or prodrugs thereof.

In some embodiments, the antioxidant is SkQ1, SkQ1H$_2$, SkQR1, SkQR1H$_2$, SkQ3, SkQ3H$_2$, SkQRB, SkQRBH$_2$, SkQB1, SkQB1H$_2$, SkQBP1, and/or SkQBP1H$_2$.

In certain embodiments, the inflammatory disorder is caused by pyelonephritis, pancreatitis, diabetes, trauma, sepsis, infection, or hepatitis. In other embodiments, the inflammatory disorder is a chronic or acute inflammatory disorder, or an autoimmune disease. In some embodiments, inflammatory disorder is caused by bronchial asthma, chronic obstructive pulmonary disease, ischemia, acute aortic dissection, kidney disease, diabetes, hyperglycemia, or bacterial infection. In some embodiments, treatment prevents disassembly of cell-to-cell contacts in an affected tissue (e.g., liver, renal, retinal, dermal, brain) caused by high glucose in the tissue, and/or prevents tissue damage by preventing neutrophils from becoming activated.

The disclosure also provides a method of lowering blood vessel permeability in a mammal suffering from a glucose metabolism disorder, comprising administering to the mammal a therapeutically effective amount of a mitochondrially targeted antioxidant having the structure:

wherein:
A is an effector moiety having a following structure:

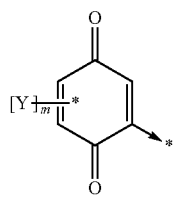

and/or reduced forms thereof, wherein:
  m is an integer from 1 to 3;
  each Y is independently selected from the group consisting of:
    lower alkyl;
    lower alkoxy; or
    two adjacent Y groups, together with carbon atoms to which they are attached, form a following structure:

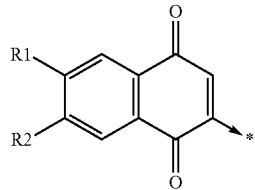

and/or reduced forms thereof; wherein:
  R1 and R2 may be the same or different and are each independently lower alkyl or lower alkoxy;
  L is a linker group, comprising:
    a) a straight or branched hydrocarbon chain which can be optionally substituted by one or more substituents and optionally contains one or more double or triple bonds; or
    b) a natural isoprene chain;
  n is integer from 1 to 40, or from 2 to 15, or from 5 to 11;
  B is a targeting group comprising $Sk^+Z^-$, wherein:
  Sk is a lipophilic cation; and
  Z is a pharmacologically-acceptable anion,
  and solvates, salts, isomers or prodrugs thereof,
thereby preventing the disassembly of endothelial cell-to-cell contact in that mammal.

In certain embodiments, the antioxidant is SkQ1, SkQ1H$_2$, SkQR1, SkQR1H$_2$, SkQ3, SkQ3H$_2$, SkQRB, SkQRBH$_2$, SkQB1, SkQB1H$_2$, SkQBP1, and/or SkQBP1H$_2$.

BRIEF DESCRIPTION OF THE DRAWINGS

The foregoing and other objects of the present disclosure, the various features thereof, as well as the invention itself may be more fully understood from the following description, when read together with the accompanying drawings, in which:

FIGS. 9A-9C are schematic representations of scans showing that augmentation of neutrophils was accompanied by a ROS burst in these cells;

FIG. 9D is a representation showing the prevention of inflammatory changes by treatment with SkQR1 ($*-p<0.01$, $**-p<0.05$);

FIG. 10A is a representation of an SDS gel showing anti-apoptotic Bcl-2 in control rats, pyelonephritic rats, and pyelonephritic rats treated with SkQR1;

FIG. 10B is a representation of an SDS gel of Bcl-2 in isolated renal mitochondria of control rats, pyelonephritic rats, and pyelonephritic rats treated with SkQR1;

FIG. 10C is a graphic representation of the results of FIG. 10A;

FIG. 10D is graphic representation of the results shown in FIG. 10B;

FIG. 15A is a representation of a scanning electron micrograph showing the lack of intercellular interaction in a co-culture of RTC and activated leukocytes, where tight-contact communications between leukocytes are shown with arrows and RTC after 24 hr co-cultivation (bar, 10 μm, 3 μm);

FIG. 15B is a representation of a scanning election micrograph showing intercellular interaction in a co-culture of RTC and activated leukocytes, where tight-contact communications between leukocytes are shown by arrows and RTC after 24 hr co-cultivation (bar, 10 μm, 3 μm);

FIG. 16 is a graphic representation showing leukocyte survival after activation with bacterial lysate measured by count of GFP-positive leukocytes in the dishes, where renal cells were co-cultivated with leukocytes carrying GFP which helped to discriminate between these two kinds of cells. Under co-cultivation conditions and the survival of activated leukocytes was higher than that observed without renal cells. ($*-p<0.01$);

DESCRIPTION

Figure 1A:
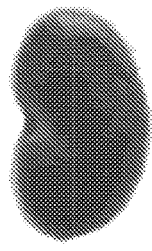
FIG. 1A is a photographic representation of a normal control kidney.

Throughout this application, various patents, patent applications, and publications are referenced. The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Mitochondrially Targeted Antioxidants (MTAs)

Mitochondria-targeted antioxidants (MTAs) have now been found to be useful in preventing and treating inflammation associated with a number of diseases, disorders, and trauma.

An MTA is a compound of the following formula:

wherein:

A is an effector moiety—antioxidant optionally having a following structure:

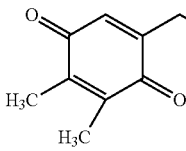

and/or reduced forms thereof, wherein:
m is an integer from 1 to 3;
each Y is independently selected from the group consisting of: lower alkyl, lower alkoxy; or two adjacent Y groups, together with carbon atoms to which they are attached, form a following structure:

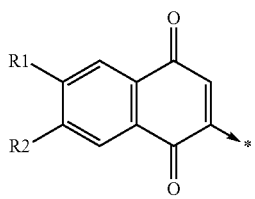

and/or reduced forms thereof; wherein:
R1 and R2 may be the same or different and are each independently lower lower alkoxy;
L is a linker group, comprising:
a) a straight or branched hydrocarbon chain which can be optionally substituted by one or more substituents and optionally contains one or more double or triple bonds; or
b) a natural isoprene chain;
n is integer from 1 to 40, or from 2 to 15, or from 5 to 11;
B is a targeting group comprising $Sk^+T^-$, wherein:
Sk is a lipophilic cation; and
Z is a pharmacologically-acceptable anion,
and solvates, salts, isomers or prodrugs thereof.

Specific useful MTAs include, but are not limited to:

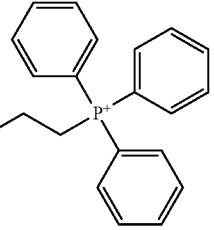

SkQ1

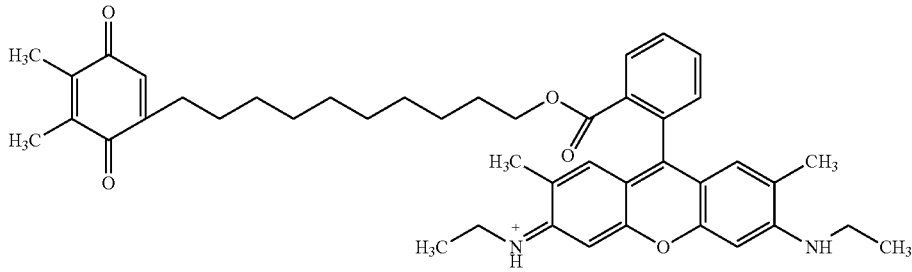

SkQR1 and their reduced (quinole) forms $SkQ1H_2$ and $SkQR1H_2$, respectively. These MTAs have been described in PCT/RU2006/000394. Other useful MTA variants include, but are not limited to SkQ3:

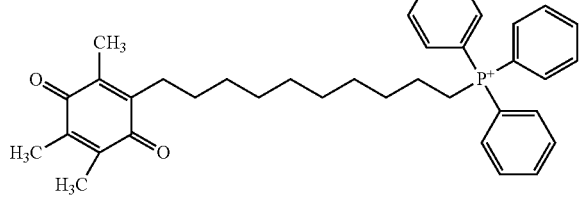

SkQ3 and its reduced (quinole) form SkQ3H$_2$; to SkQRB:

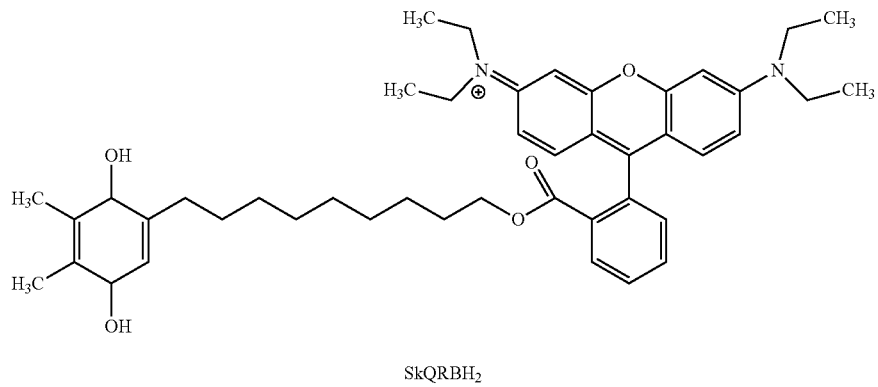 [SMILES: CCN(CC)c1ccc2c(-c3ccccc3C(=O)OCCCCCCCCCC3=CC(O)C(C)=C(C)C3O)c3ccc(=[N+](CC)CC)cc-3oc2c1]

SkQRBH$_2$ and its oxidized (quinine) form SkQRB;
to SkQB1:

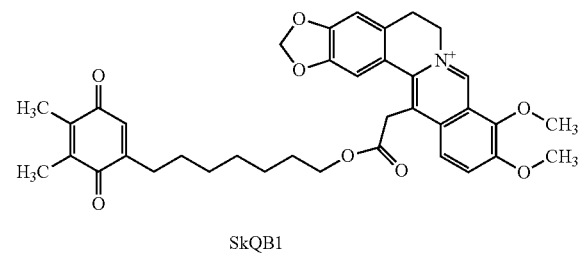

SkQB1 and its reduced (quinole) form, SkQB1H$_2$; and
to SkQBP1:

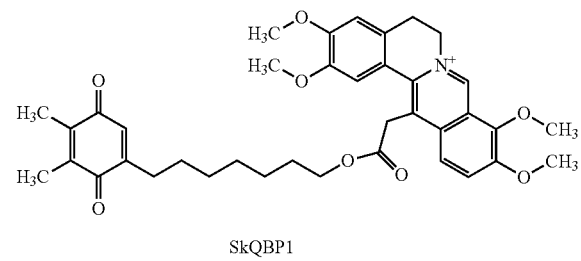

SkQBP1 and its reduced (quinole) form SkQBP1H$_2$.

These MTAs are useful in preventing and treating inflammatory pathologies, at least in part, by reducing or preventing inflammation-induced tissue damage. Such pathologies include, but are not limited to pyelonephritis, pancreatic, diabetes and other glucose metabolism disorders, hepatitis, chronic obstructive pulmonary disease, ischemia, acute aortic dissection, kidney disease, trauma, bacterial infections, acute inflammatory disorders, sepsis, and autoimmune disorders such as, but not limited to bronchial asthma.

Pyelonephritis Models

Pyelonephritis was studied as an exemplary inflammatory pathology because mitochondrial ROS is a source of kidney cell damage in experimental APN in both a conventional in vivo model based on the inoculation of bacteria into the bladder, and in a novel in vitro model of inflammation based on the interaction of pathogen/endotoxin-activated leukocytes with cultured kidney epithelial cells. As a result of this stress, the progression of oxidative stress has been observed in renal cells in vitro and their death. This oxidative stress was caused by leukocytes generating ROS which is initiated by interaction with bacterial antigens. After activation, leukocytes excrete to the exterior ROS, NO, and TNF. The suppression of leukocytic NADPH oxidase yielded a dramatic decrease of ROS within renal cells which may serve as an argument to support the idea that leukocytes are specifically responsible for excessive ROS production in the pyelonephritic kidney.

Protective effects of mitochondria-targeted antioxidants (MTAs) (for example SkQ1 and SkQR1) were demonstrated (Example 1). MTA treatment prevented the achievement of a "point of no return" in the path toward cell death (Kroemer et al. (1995) *FASEB J.* 9:1277-1287).

Renal cell protection afforded by SkQ1 and SkQR1 was more pronounced than that afforded by the traditional water-soluble antioxidant, Trolox. This demonstrates the role of targeting an antioxidant into mitochondria in the prevention of onset and propagation of renal pathology. Importantly, these MTAs did not have an effect on the level of TNFα production by leukocytes exposed to bacterial lysate, suggesting that MTAs do not suppress certain stages of inflammation. Thus, targeting mitochondrial ROS is beneficial under conditions of an ongoing infection where traditional anti-inflammatory drugs may interfere with microbial clearance.

Mitochondria-mediated oxidative stress in renal cells injury in an in vivo model of experimental APN has been determined to have a role. In one study, MDA, which is an indicator of lipid peroxidation (Cherubini, et al. (2005) *Free Radic. Biol. Med.* 39:841-852; Gupta et al. (1996a) *FEMS Immunol. Med. Microbiol.* 13:35-42), was elevated in the kidneys of rats with experimental APN, indicating oxidative renal damage.

In addition, higher levels of ROS generation were observed in blood leukocytes of pyelonephritic rats. The mitochondria-targeted antioxidant SkQR1 normalized ROS level in blood leukocytes and in the kidneys of pyelonephritic animals. SkQR1 treatment also suppressed neutrophils infiltration in the diseased kidney as well as the level of TNFα in the tissue showing the high efficacy of mitochondria-targeted antioxidants in preventing inflammation injury in the kidney.

When the titer of bacteria injected into the bladder was high, a high level of deaths was observed among experimental animals, which, together with high level of TNFα and bacteremia, gave strong evidence of a septic progression. MTAs significantly increase survival of animals with severe APN.

The renal damage following APN is mainly caused by the inflammatory process associated with the infection, rather than by the direct effect of bacteria on the kidney (Bennett et al. (1999) *J. Urol.* 161:1681-1684); Haraoka et al. (1994) J. Urol. 151:1078-1080); Imamoglu et al. (2006) *Urology* 67:1315-1319). Bacterial invasion of the host kidney triggers the innate immune system. After recognition of bacteria, toll-like receptor signaling (Shirali and Goldstein, (2008) J. Am. Soc. Nephrol. 19:1444-1450) initiates an immune response involving nuclear factor κB and the production of cytokines and chemokines (Li et al. (2002) *Respir. Res.* 3:23; Ragnarsdottir et al. (2008) *Eur. J. Clin. Invest.* 38(Suppl.)2:12-20; Tullus et al. (1997) *Acta Paediatr.* 86:1198-1202).

It was determined that in the leukocyte culture medium from pyelonephritic rats, the level of TNFα increased with time, and that this medium, itself, could cause oxidative stress in renal cells. Both in the in vitro model, and under conditions of experimental APN, a significant elevation of the level of toll receptors in both kidney cells and leukocytes was observed. Treatment with the MTA, SkQR1, resulted in normal expression of these receptors in different regions of the kidney, activated under APN. Apart from this, the onset of APN is associated with activation of pro-inflammatory signaling pathways in peripheral leukocytes. This activation was suppressed in SkQR1-treated rats.

Figure 11:
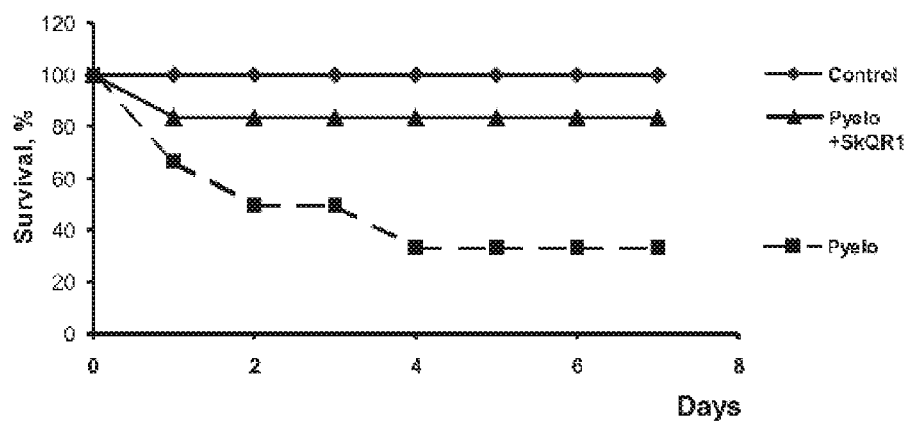
FIG. 11 is a graphic representation of the survival rates of control rats, pyelonephritic rats, and pyelonephritic rats treated with SkQR1.

A model of the pathological events occurring around and within the pyelonephritic renal cell is shown in FIG. 11. This model explains the incidence of inflammatory cell damage and death. An element in this model is the role of mitochondrial ROS in all steps of the pathological progression. In a majority of pathological (intermediate) steps, pro-death and pro-survival signaling is related to mitochondrial function, MTAs are effective anti-pyelonephritic drugs with high potency to prevent scarring and renal dysfunction in the cases where direct antibacterial measures are restricted (in children, pregnant women, individuals with primary immunodeficiency, etc.) or inefficient (in cases of antibiotic-resistant bacterial strains).

Host defense against infection can be achieved through resistance and tolerance mechanisms (Medzhitov et al. (2012) *Science* 335:936-941). The present study (e.g., Example 1) demonstrates that mitochondrial ROS are an important contributor to inflammation-induced tissue damage, and that targeting mitochondrial ROS can improve survival of the host during otherwise lethal bacterial infections.

Effect of MTAs on Blood Vessels Permeability

As shown in Example 2, SkQ1 treatment prevented disassembling of endothelial cell-to-cell contacts caused by high glucose treatment. This was determined by immunoblotting analysis of VE-cadherin). Endothelial cell-to-cell contacts are readily disassembled under a variety of pathological conditions including diabetes, traumas, sepsis and other inflammatory diseases. This leads to increased blood vessel permeability and may result in life-threatening condition. therefore, vessel permeability should be lowered under these circumstances. SkQ1 was shown to be effective in protecting endothelial cells and vessels against high glucose and inflammatory cytokines in circulating blood, thus SkQ1 is useful for prevention and treatment of pathological conditions caused by glucose metabolism disorders including diabetes and hyperglycemia, sepsis, trauma as well as chronicle and acute inflammatory diseases.

Effect of MTAs on Neutrophil Activation

Example 2 also shows that SkQ1 treatment prevents human neutrophil activation caused by fMet-Leu-Phe which is a bacterial product analog (as determined by zymography analysis). This finding was unexpected since human neutrophils contain small amounts of mitochondria having very low metabolic activity.

Human neutrophils are activated by components of pathogens and disrupted human cells, as well as proinflammatory cytokines. MMP-9 is a metalloproteinase released from activated neutrophils. Excess neutrophil activation leads to massive tissue damage. Activated MMP-9 is known to be involved in bronchial asthma and chronic obstructive pulmonary disease (Takafuji et al. (2003) *J. Investig. Allergol. Clin. Immunol.* 13:50-55), ischemia (Gidday et al. (2005) *Am. J. Physiol. Heart Circ. Physiol.* 289:558-568), acute aortic dissection (Kurihara et al. (2012) *Circulation.* 126: 3070-3080), kidney disease, trauma, sepsis, inflammation, and many other disease and pathological conditions attended by tissue remodeling.

The data provided herein demonstrates the tissue damage associated with MMP-9 release from activated human neutrophils. SkQ1 was shown to be effective in protecting human tissues against MMP-9 related damage and damage caused by pathogens and/or inflammatory cytokines. Thus, SkQ1 is useful for prevention and treatment of bronchial asthma, chronic obstructive pulmonary disease, ischemia, acute aortic dissection, kidney disease, trauma, sepsis, and other inflammatory diseases.

Effect of MTAs on Other Inflammatory Models

The protective effect of MTAs was also demonstrated in a model of hepatitis (Example 4) and a in model of pancreatitis (Example 5).

Reference will now be made to specific examples illustrating the invention. It is to be understood that the examples are provided to illustrate certain embodiments and that no limitation to the scope of the invention is intended thereby.

EXAMPLES

Example 1

Protective Effect of MTAs in the Model of Acute Pyelonephritis

A. Experimental Procedures

1. Primary Rat Kidney Cell Culture

Kidneys from 1-3 day old rats were excised under aseptic conditions. The tissue was blended and dissociated by collagenase treatment (0.5%, 30 min at 37° C.). The final suspension was centrifuged for 5 min at 50 g. The pellet was resuspended in about 10 ml of DMEM/F12 (Gibco, USA) supplemented with 10% FCS (Gibco, USA) and kept for 2 min, after which the supernatant was transferred to another tube and the pellet was repeatedly resuspended. After 10 min, the renal tubules were pelleted and dissociated cells remaining in the suspension were discarded. The pellet was resuspended in DMEM/F12 with 10% FCS and seeded onto 24-well plates or onto coverslips placed in 35-mm glass-bottom Petri dishes.

2. Cultivation of Bacteria

*E. coli* strain No. 85 was cultured overnight in a cultivation medium containing 1% tryptone, 0.5% yeast extract and 1% NaCl (Sigma-Aldrich, USA). The medium, containing roughly $10^9$ colony-forming units (CFU) per ml, was pelleted at 300 g for 3 min. The bacterial lysate was prepared by diluting 30 ml of an overnight (ON) culture and diluting the precipitate in 3 ml of 0.9% NaCl followed by autoclaving for 1.5 hr at 120° C.

3. Preparation of Leukocytes from Peripheral Blood 5 ml heparinized blood collected from the jugular vein of adult male rats was carefully layered over 5 ml of Ficoll-Urografin (density of 1.077 g/cm$^3$), and centrifuged for 30 min at 200 g. This procedure results in erythrocyte pelleting, while the mononuclear fraction of leukocytes forms an interphase ring on the Ficoll surface, which was carefully collected. Leukocytes were transferred into another tube and centrifuged for 3 min at 200 g. The resultant pellet was resuspended in 5 ml of DMEM/F12. After cell counting in a hemocytometer, the cells were diluted to a final concentration of about $1\times10^5$ cells per ml.

For preparation of neutrophils, the proper fraction from a Ficoll gradient was transferred to another tube, mixed with 10 ml of DMEM/F12 and centrifuged for 3 min at 200 g. The final pellet containing neutrophils was resuspended in 5 ml of DMEM/F12, the cells were counted and then diluted to a final of about $1\times10^5$ cells per ml.

The same procedure was applied to obtain leukocytes from GFP-mice.

4. Inflammation Modeling in vitro

In a two-day old renal cell culture, the medium was substituted with DMEM/F12 (400 µl per well, 1600 µl per dish), supplemented with (depending on the purpose): GSK-3β inhibitor LiCl (9 mM) (Sigma-Aldrich, USA), water-soluble antioxidant Trolox (50 µM, 100 µM) (Sigma-Aldrich, USA), MTAs 10-(6-plastoquinonyl)decyl-triphenylphosphonium (SkQ1), synthesized according to Antonenko et al. (2008) *Biochemistry (Mosc)* 73:1273-87), 10 nM, 100 nM), and 10-(6'-plastoquinonyl) decylrhodamine 19 SkQR1), synthesized according to Antonenko (2008), (1 nM, 10 nM, or 100 nM). Renal cells were incubated for 2 hr in this medium, followed by supplementation with leukocytes or neutrophils in DMEM/F12, or DMEM/F12, alone, in the control sample (400 µl per well, 1600 µl per dish). Simultaneously, the bacterial lysate or lipopolysaccharide (100 ng/ml, LPS, Sigma-Aldrich, USA) solution in DMEM/F12 and DMEM/F12 alone in the control sample (100 µl per well, 400 µl per dish) were added. Renal cells, leukocytes (neutrophils) were co-cultivated for 24 or 48 hr with bacterial lysate or LPS. Cell death (both necrotic and apoptotic) rate was evaluated using Annexin-V FITC Kit (Invitrogen, USA).

5. In vivo Rat Model of APN

An in vivo experimental model of APN was used where bacteria are introduced in the bladder of rat (Gupta et al. (1995) *J. Med. Microbiol.* 43:33-36). Experiments were performed on outbred white female rats (180-200 g) fed ad libitum. Animal protocols were approved by the Institutional Review Boards. Rats were anesthetized with chloral hydrate (300 mg/kg, intraperitoneally(ip)). The animals were infected intraurethrally using a soft Intramedic non-radio-opaque polyethylene catheter (Clay Adams, USA). The inoculum (5 ml per kg, $1\times10^8$ CFU/ml of rat fecal bacterial composition) was injected slowly to avoid any leakage into the bladder. Control animals were untreated. The therapeutic protocol of SkQR1 used to treat this pathology was as follows: ip injection of SkQR1 (100 nmoles/kg of body weight) 1 hr after injection of bacteria, with subsequent injections of the same amount of SkQR1 at 12, 24, 36 and 48 hrs; in total, each animal received 500 nmol SkQR1 per kg.

On the second day after the injection, blood samples were taken and kidneys were excised for the mitochondria isolation, determination of MDA level in the tissue, Western blotting and histopathological examination.

Kidney mitochondria were isolated by homogenization and differential centrifugation in a medium containing 250 mM sucrose, 20 mM HEPES-KOH, 1 mM EGTA and 0.1% BSA, pH7.4. Total mitochondrial protein was determined using a bicinchoninic acid protein assay kit (Sigma-Aldrich, USA). The mitochondria from cultured kidney cells were isolated by the same protocol.

6. Measurements of ROS, NO, MDA and TNFα

The ROS-sensitive fluorescent probe 2,7-DCF-DA (Molecular Probes, USA) dissolved in DMEM/F12 without bicarbonate (final concentration 10 µM) was added to renal cells (500 µl per well of 24-well plate, 2 ml per dish) and incubated for 15 min at 37° C. followed by a wash with DMEM/F12 without bicarbonate. MDA was determined as in (Mihara and Uchiyama (1978) *Anal. Biochem.* 86:271-8). Fluorescent probe, DAF-2-DA (Calbiochem, San Diego, Calif., USA) was used for NO determination in living cells. The procedure was the same as for 2,7-DCF-DA. The nitrite/nitrate concentration (as products of NO oxidation) in culture media was determined using Nitrite/Nitrate Assay Kit (Sigma-Aldrich, USA). TNFα was determined using the kit Rat TNFα ELISA Ready-SET-Go (Ebioscience, USA).

7. Confocal and Scanning Electron Microscopy

Renal cells were imaged with an LSM510 inverted confocal microscope (Carl Zeiss Inc., Jena, Germany) with excitation at 488 nm and emission collected at 500 nm-530 nm with a pinhole diameter of 150 µm. Images were processed using ImageJ software (NIH, Bethesda, Md., USA).

For scanning electron microscopy, cells and bacteria were fixed in 2.5% glutaraldehyde in $Ca^{2+}$ and $Mg^{2+}$-free Hanks buffer supplemented with 5 mM EDTA, 5 mM phenylmethylsulfonyl fluoride and 10 mM HEPES at pH 7.3. Cells were postfixed with 1% osmium tetroxide in 0.1 M sodium cacodylate with 0.1 M sucrose at pH 7.3 (without replacing a buffer containing glutaraldehyde), dehydrated in acetone series, critical-point-dried with liquid $CO_2$ as a transitional fluid in a Balzers apparatus, sputter-coated with gold-palladium and observed at 15 kV with a Camscan S-2 or JSM-6380 scanning electron microscope.

8. Renal Histology and Grading of Inflammatory Tissue Damage

The kidney was isolated immediately after sacrificing the animal and perfused with ice-cold PBS. It was then fixed in a 10% neutral buffered formalin solution, embedded in paraffin and used for histopathological examination. Five micrometer thick sections were cut, deparaffinized, hydrated, and stained with hematoxylin and eosin. The renal sections were examined in blinded fashion for inflammation and infiltration by leukocytes in the kidneys of all treated animals. A minimum of 10 fields for each kidney slide were examined and scored for pathologic severity.

The manifestation of inflammatory indicators (i.e., a number of infiltrated leukocytes in every layer and the presence of abscesses) under APN was evaluated using the following scale: 0, none; 1, 5-50 leukocytes in the view field; 3, >100 in a view field; 4, abscesses with pus-necrotic content. The distribution of inflammatory changes (i.e., comparative analysis of infiltration and abscesses) was evaluated by the following criteria: 0, none in any layer; 1, infiltration in the medullar layer; 2, infiltration reaching the cortex.

9. Myeloperoxidase Activity Assay

Kidney homogenates for MPO determination were centrifuged at 20000 g 15 min, the pellets were resuspended in 50 mM K-phosphate buffer containing 0.5% CTAB. Resulted samples were frozen and thawed three times and then centrifuged at 10600 g 10 min. Supernatants were analyzed for MPO activity in chromogenic reaction with o-phenylenediamine (OPD). 100 µl sample was mixed with 100 µl substrate buffer (25 mM Na-citrate, 50 mM Na-phosphate, 0.45 mg/ml OPD, 0.1% $H_2O_2$, pH 5.0) and was incubated 15 min at room temperature and then OD was detected at 492 nm.

10. Immunocytochemistry

Cells and kidney slices were washed in PBS, fixed for 30 min in 4% formaldehyde with PBS at 4° C., and permeabilized in PBS containing 0.02% Triton X-100 for 60 min at 4° C. (0.5 ml per well, 5 ml per slice), followed by blocking in PBS with 0.5% bovine serum albumin (PBS-BSA) for 60 min at room temperature (0.5 ml per well, 2 ml per slice). After three 15-min rinses in PBS-BSA, cells were incubated for 1 hr with secondary antibodies diluted 1:200 (FITC-conjugated anti-rabbit IgG, Jackson ImmunoResearch Laboratories, USA). The kidney slices and coverslips with attached cells were washed, placed on microscope slides with a mounting medium and sealed beneath coverslips. Confocal microscopy images were processed using ImageJ software (NIH, Bethesda, Md., USA).

11. Western Blot Analysis

Samples of kidney homogenates were loaded onto 15% Tris-glycine polyacrylamide gels (10-20 µg of total protein per lane). After electrophoresis, gels were blotted onto PVDF membranes (Amersham Pharmacia Biotech, UK). Membranes were blocked with 5% (wt/vol) non-fat milk in PBS with 0.1% (vol/vol) Tween 20 and subsequently incubated with appropriate primary antibodies. Membranes were then treated with corresponding anti-mouse or anti-rabbit secondary antibodies. Specific bands were visualized using ECL Plus Western blotting kit (Amersham Pharmacia Biotech, UK). After scanning, the density of the resulting staining in the membrane was measured for each band using ImageJ software (NIH, Bethesda, Md., USA).

12. Statistics

All experiments were performed at least in triplicates. All data are presented as mean±SEM. Comparisons between groups were made using a Student t test with a P value less than 0.05 taken to indicate statistical significance.

B. Results

1. Effect of MTA SkQR1 on an APN-Induced Oxidative Stress in the Tissue

Figure 1B:
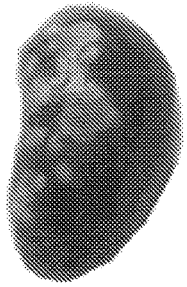
FIG. 1B is a photographic representation of a kidney with pyelonephritis.
Figure 1C:
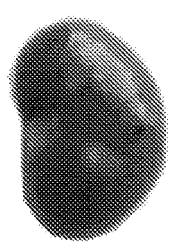
FIG. 1C is a photographic representation of a kidney with pyelonephritis treated with SkQR1.
Figure 2A:
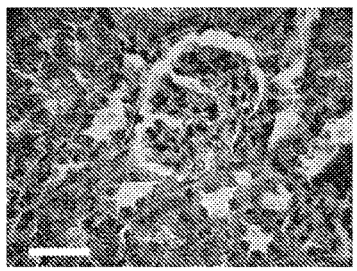
FIG. 2A is a photographic representation of a histological section of control rat cortex stained with hematoxylin and eosin.
Figure 2B:
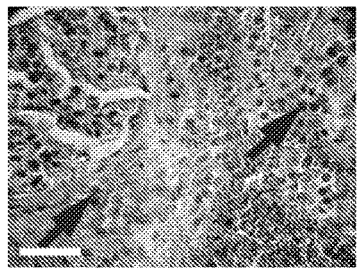
FIG. 2B is a photographic representation of a histological section of renal cortex from a rat with pyelonephritis.
Figure 2C:
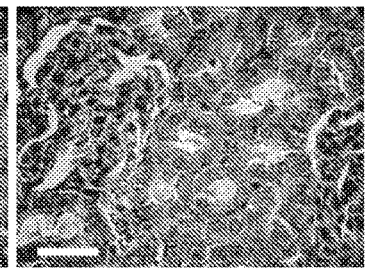
FIG. 2C is a photographic representation of renal cortex from a rate with pyelonephritis treated with SkQR1.
Figure 3A:
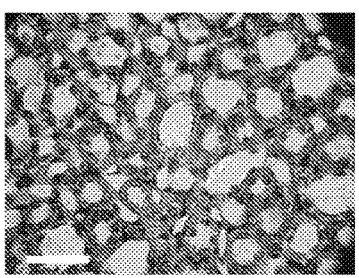
FIG. 3A is a photographic representation of a histological section of a control medulla stained with hematoxylin and eosin.
Figure 3B:
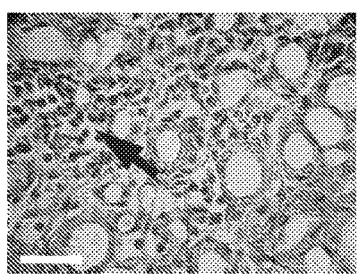
FIG. 3B is a photographic representation of a histological section of a control medulla with pyelonephritis stained with hematoxylin and eosin.
Figure 3C:
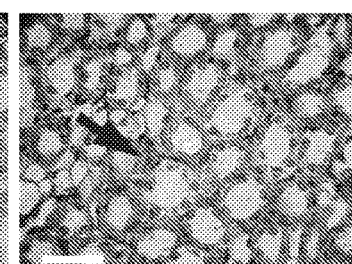
FIG. 3C is a photographic representation of a histological section of a control medulla with pyelonephritis treated with SkQR1.
Figure 4:
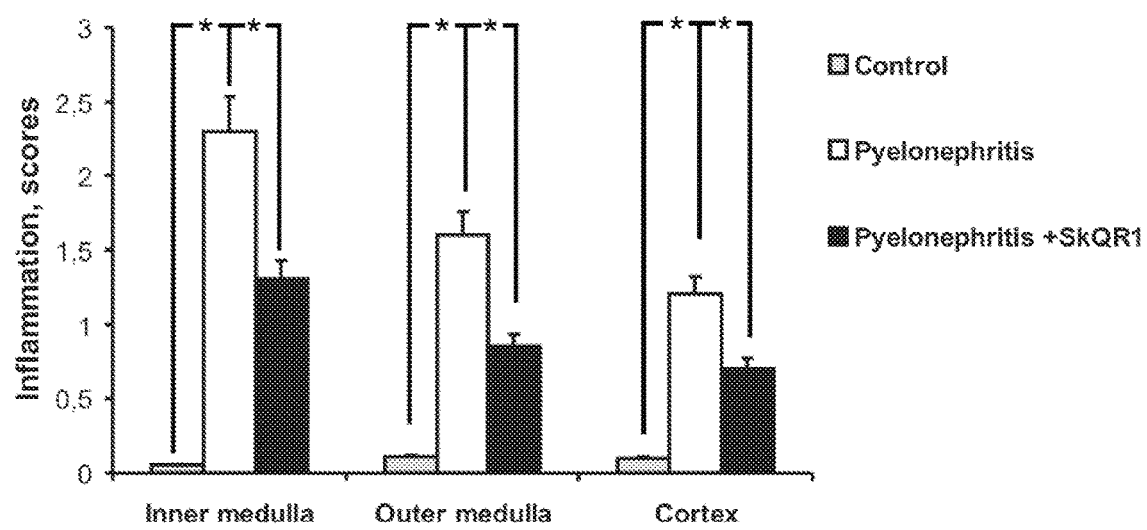
FIG. 4 is a graphic representation showing the inflammation index (see methods) in medulla and renal cortex presented in FIGS. 2 and 3.

A number of signs of inflammation and oxidative kidney tissue damage were observed in the APN model (FIGS. 1A-1C). The kidneys of pyelonephritic rats (FIG. 1B) showed a great number of abscesses, which were significantly less prevalent in rats treated with SkQR1 (FIG. 1C). An extensive leukocyte infiltration of the kidney took place (FIGS. 2 and 3). Interstitial infiltrates sometimes were local but often covered significant part of the kidney parenchyma and originated almost exclusively from invaded polymorphonuclear leukocytes (neutrophils). In some loci, infiltrates embraced blood vessels. Severe and characteristic changes were revealed in kidney tubules as well: they were swollen, their cells were degenerated and often peeled off to the tubular lumen. Often the tubules were filled with a pus-necrotic and bacterial content. Pathological changes were mostly observed in the medullar part of the kidney (FIGS. 2-4). The glomeruli and cortical tubules in the majority of cases were relatively intact. Importantly, treatment with SkQR1 inhibited both leukocyte infiltration in all kidney layers and the spreading of the inflammatory process (FIGS. 2-4).

Figure 5A:
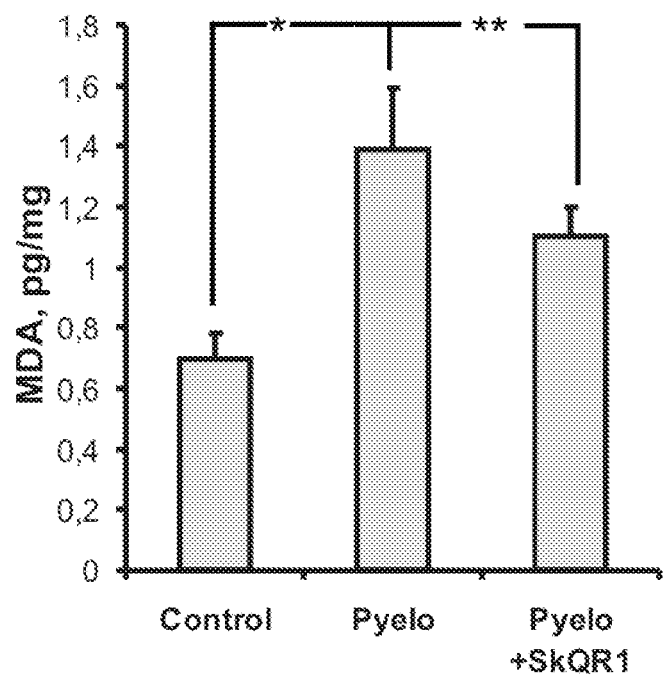
FIG. 5A is a graphic representation of inflammation in the kidney accompanied by oxidative stress, as measured by MDA accumulation in the tissue.

The concentration of peroxidative products such as malonyldialdehyde (MDA), an index of oxidative stress in the whole kidney tissue, was elevated after induction of APN (FIG. 5A) demonstrating remarkable oxidative tissue damage. MDA concentration was significantly lower in animals receiving SkQR1 (FIG. 5A), demonstrating the protection of the kidney tissue from oxidative stress afforded by this mitochondria-targeted antioxidant.

Figure 5B:
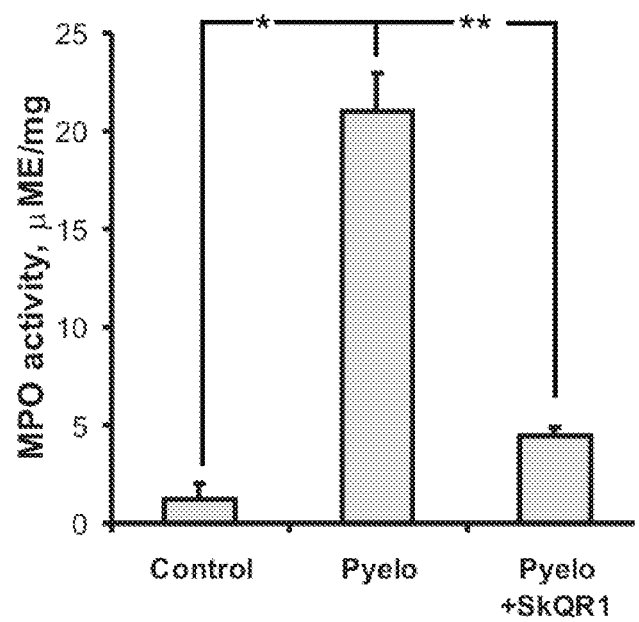
FIG. 5B is a graphic representation of inflammation in the kidney accompanied by oxidative stress as measured by MPTO activity (bar, 50 μm, *–p<0.01, **–p<0.05)

Tissue activity of myeloperoxidase (MPO), an index of neutrophil infiltration, was severely elevated in pyelonephritic kidneys but again significantly inhibited in rats treated with SkQR1 (FIG. 5B).

2. Oxidative and Nitrosative Stress and Renal Cells Death

Figure 6A:
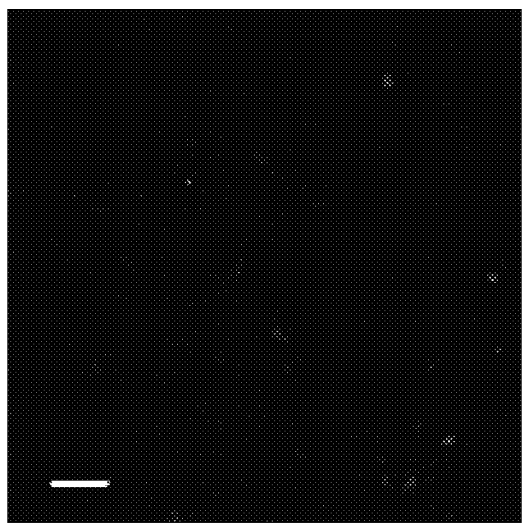
FIG. 6A is a representation of a confocal micrograph of control renal tubular cells (RTC) stained with DCF-DA (bar, 50 μm) not showing any visible DCF fluorescence.
Figure 6B:
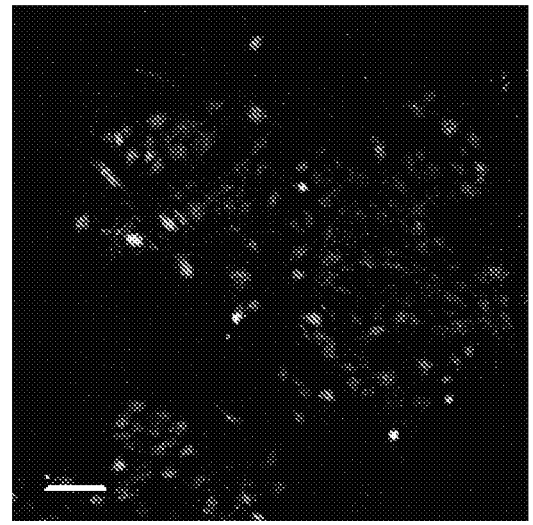
FIG. 6B is a representation of control renal tubular cells (RTC) incubated with activated leukocytes (LC)+bacterial lysate (BL) and stained with DCF-DA (bar, 50 μm), showing enhanced fluorescence.

Mitochondria-mediated oxidative stress was studied in the cellular model of pyelonephritis in which renal tubular cells (RTC) are co-cultivated with antigens (bacterial lysate-activated leukocytes). Using this model a significantly greater fluorescent signal from DCF was observed, which indicates antigen-mediated ROS production (FIG. 6B), than in controls (FIG. 6A). Specifically, the ROS level was about 5 times higher than in the control (untreated) cells, which is in agreement with the assumption that initiation of oxidative stress in renal cells is mediated by activated leukocytes. Non-activated leukocytes also caused the increase in ROS production in the RTC (not shown) but it was almost twice less than in the case of activated leukocytes; this can be explained by possible activation of leukocytes during the process of their preparation. Confocal microscopy confirmed that the higher ROS signal detected in activated leukocyte-renal cell co-culture originated mainly from the renal cells (FIG. 6B).

Figure 7A:
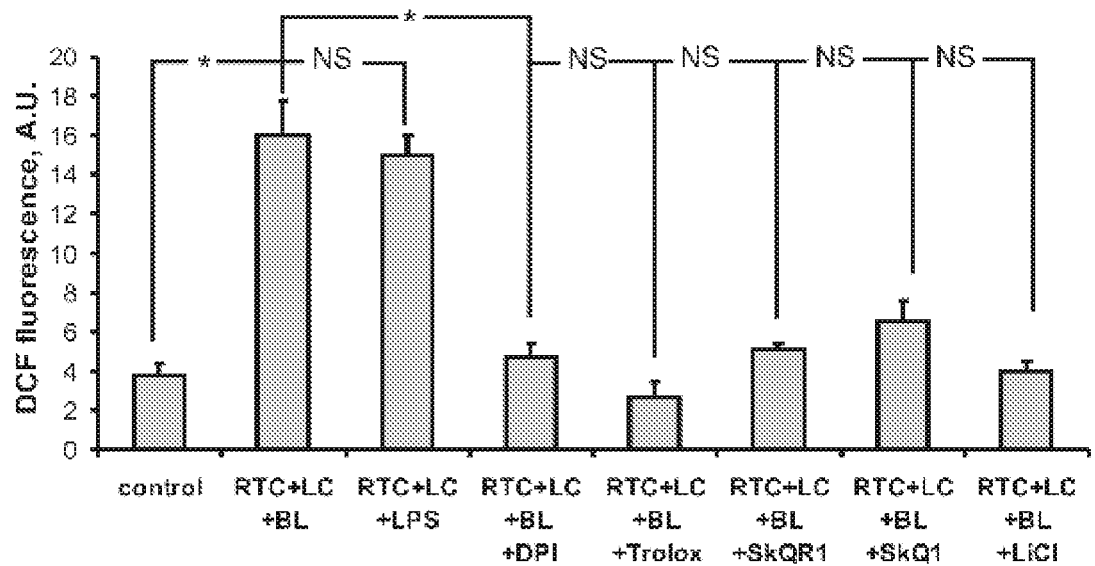
FIG. 7A is a graphic representation showing the quantitative results and effects of RTC treated in different ways and stained with DCF-DA (bar, 50 μm)

Pure LPS isolated from the bacterial cell wall is commonly used for leukocyte stimulation (Sakaguchi et al. (2007) *Int. Immunopharmacol.* 7:191-197). The effects of LPS and bacterial lysate were compared. The application of LPS also caused leukocyte activation and greater ROS level in the renal cells (FIG. 7A). Specifically, 100 ng/ml of LPS had the same effect as was observed with bacterial lysate. However, the utilization of bacterial lysate is more appropriate in terms of imitation of in vivo conditions after initiation of pyelonephritis. Bacterial lysates have been shown to be more efficient than bacteria-derived soluble products for the induction of an activating phenotype in human dendritic cells. The present experiments with a specific inhibitor of NADPH oxidase, diphenyleneiodonium (DPI) (0.5 µM) (Morandi et al. (2011) *Immunol. Lett.* 138:86-91) demonstrated that this enzyme is responsible for the primary and/or the secondary ROS production in this system, since DPI inhibited the ROS production inside renal cells (FIG. 7A).

To prevent the oxidative stress in renal cells as well as to diminish cell death, three drugs with potent antioxidative capacity were used: Trolox, a water soluble analog of vitamin E, and MTAs SkQ1 and SkQR1. Treatment with each of these resulted in dramatically lower ROS production levels in renal cells (FIG. 7A), Pretreatment of renal cells with 10 nM SkQ1, 10 nM SkQR1, or 100 µM Trolox for 2 hr resulted in suppression of ROS production after co-cultivation with activated leukocytes to levels close to those observed on controls. Similarly, LiCl pre-treatment also had an antioxidative effect (FIG. 7A).

Figure 7B:
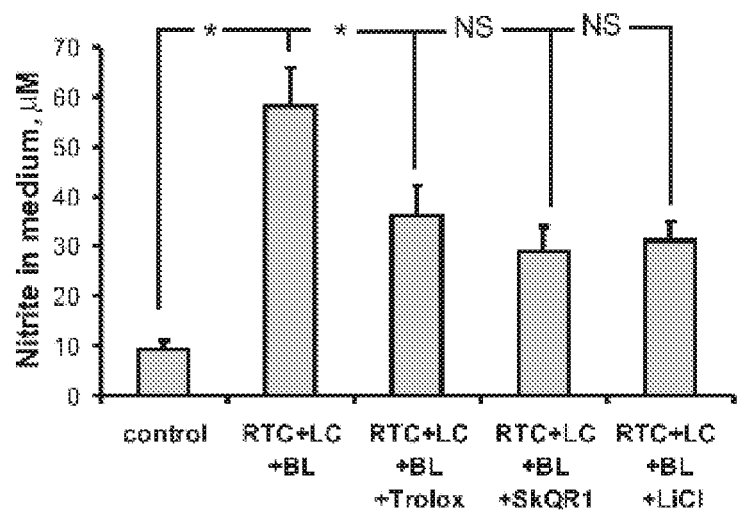
FIG. 7B is a graphic representation showing the nitrite concentration as an indicator of total NO production in RTC treated in different ways.
Figure 7C:
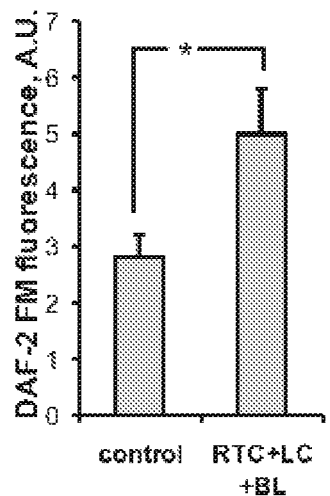
FIG. 7C is a graphic representation of the generation of NO in RTC as measured by DAF-2FM fluorescence in RTC treated in different ways.

In addition to ROS, leukocytes activated by an antigen may produce a substantial amount of NO. After incubation of kidney cells with leukocytes and bacterial lysate for 24 h, the level of nitrate/nitrite (basic products of NO oxidation) in the medium was greater by more than 5-fold than in controls (FIG. 7B). However, the effect of leukocyte activation on NO production in kidney cells, when measured by fluorescence of DAF-2, seems to be much less prominent (FIG. 7C). Nitrosative stress shows a less profound response to leukocyte activation than oxidative stress. Nevertheless, pre-incubation with three different drugs revealed some suppression of nitrate/nitrite accumulation (FIG. 7B).

Figure 7D:
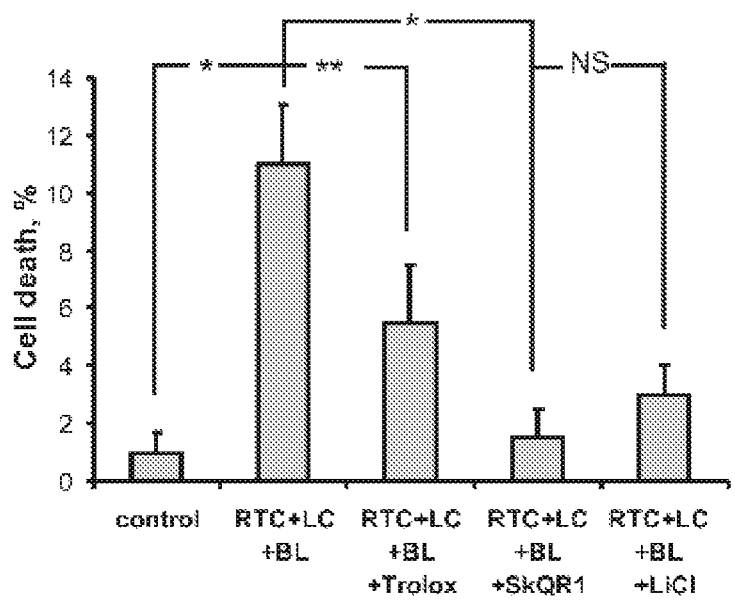
FIG. 7D is a graphic representation of RTC cell death and protective effects of some drugs (*–p<0.01, **–p<0.05)

In the present cellular model of pyelonephritis, substantial renal cell death was seen after 48 hr of exposure to activated leukocytes (more than 10% of renal cells became Annexin V-positive. Pre-incubation with three different drugs was protective, with SkQR1 showing the highest efficiency (FIG. 7D). Comparison of the protective effects of SkQR1 and Trolox on the level of oxidative stress (FIG. 7A) and on cell death (FIG. 7A) demonstrates the distinct effects of these compounds. Specifically, the MTA showed the highest potency in protection against renal cell death. Similarly, LiCl also protected renal cells from death and its effect was more profound than of Trolox.

3. Effect of TNF on Oxidative Stress in the Kidney

Figure 12:
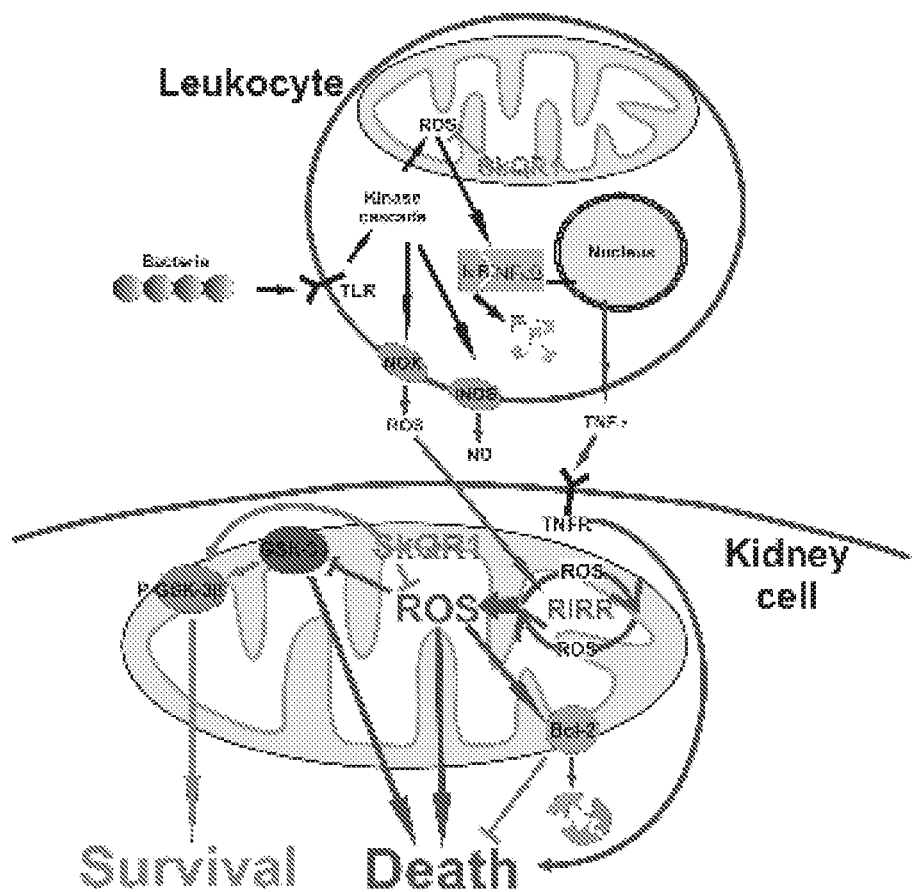
FIG. 12 is a diagrammatic representation of the scheme of changes in leukocyte and renal cells and their mitochondria after bacterial invasion (blue=pro-survival and red=pro-death elements). NOX=NADPH oxidase; iNOS, inducible NO-synthase; TNFR, the receptor for TNF-α; RIRR, ROS-induced ROS release cascade; P-GSK-3β and GSK-3β, pro-survival (phosphorylated) and pro-apoptotic (dephosphorylated) forms of glycogen synthase kinase 3β.
Figure 13A:
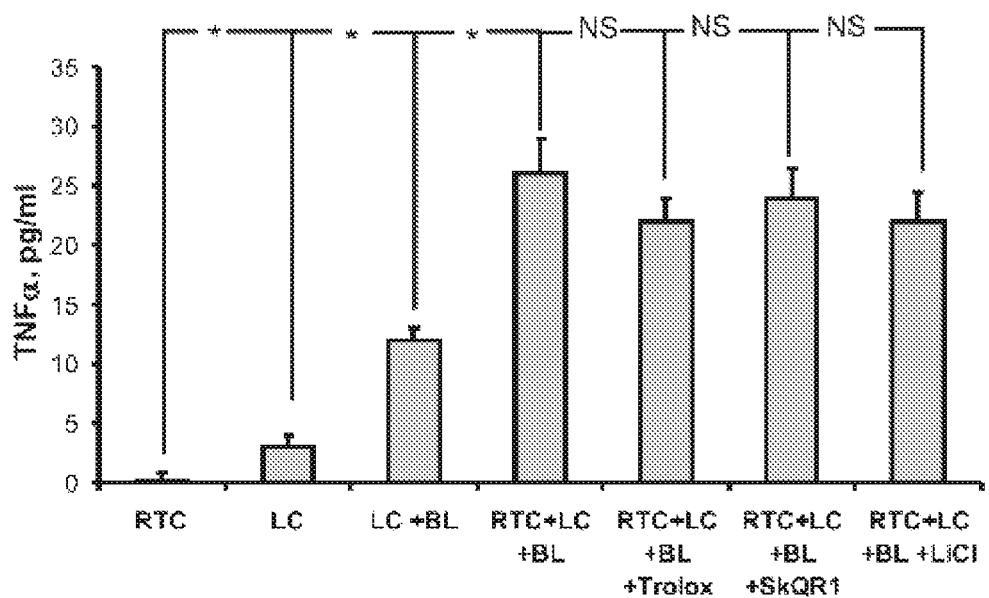
FIG. 13A is a graphic representation of the production of TNFα in a co-culture of RTC and activated leukocytes (LC+BL) not treated or treated with Trolox, SkQR1, and showing that the production of TNFα was significantly higher in activated LC, as compared to control LC, especially in co-culture with RTC while incubation with the indicated drugs had no effect.

Bacterial lysate induced a robust TNF production by leukocytes (FIG. 12A). Interestingly, TNF release in the medium was even higher after co-culture of activated leukocytes with renal cells (FIG. 13A) which points to the role of renal cell-leukocyte interaction in the induction of inflammation. Trolox, LiCl and SkQR1 did not have a significant effect on the TNF release in RTC-leukocyte co-culture.

Figure 13B:
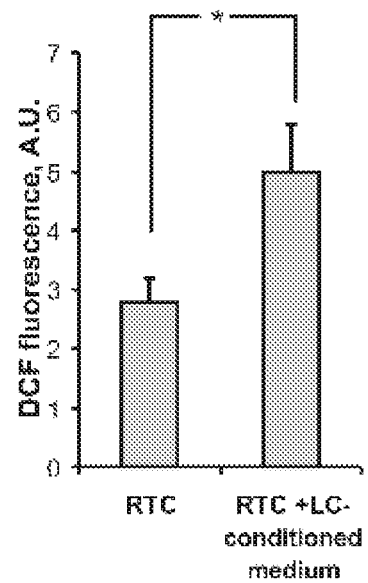
FIG. 13B is a graphic representation of the production of TNFα in the RTC in normal and LC-conditioned medium as measured by DCF fluorescence ($*-p<0.01$)

Whether released TNF itself can affect renal cells by inducing oxidative stress was then tested. For this purpose, the medium, in which leukocytes were treated with bacterial lysate, was centrifuged and added to renal cells. TNF-containing medium was found to increase ROS level in renal cells, although to a lesser extent compared to that observed after co-cultivation of renal cells and activated leukocytes (compare FIG. 7A and FIG. 13B). Thus, the direct interaction of renal cells and co-cultivated leukocytes play an important role in the induction of oxidative stress in renal cells.

4. Oxidative Stress and Changes in Blood Leukocytes

Figure 8A:
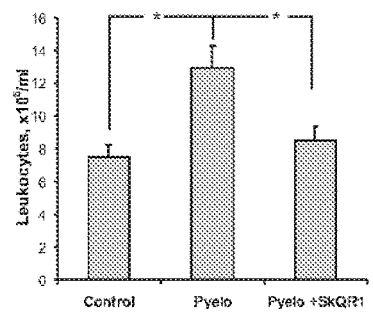
FIG. 8A is a graphic representation of elevated blood leukocyte counts in control rats, pyelonephritic rats, and in pyelonephritic rats treated with SkQR1.
Figure 8B:
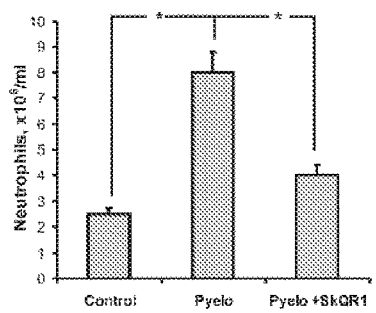
FIG. 8B is a graphic representation of elevated neutrophil counts in control rats, pyelonephritic rats, and pyelonephritic rats treated with SkQR1.
Figure 8C:
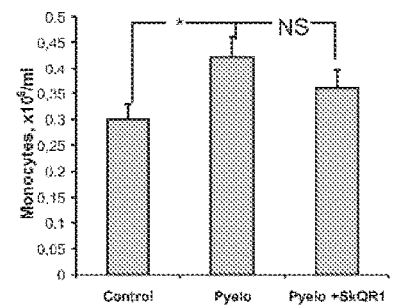
FIG. 8C is a graphic representation of the monocyte concentration in the blood of control rats, pyelonephritic rats, and pyelonephritic rats treated with SkQR1 ($*p<0.05$ vs. control; $**p<0.05$ vs. APN group)
Figure 8D:
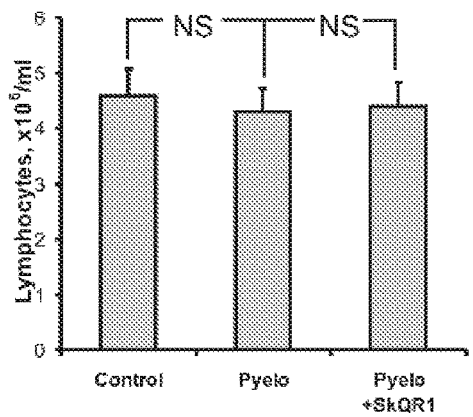
FIG. 8D is a graphic representation of the level of lymphocytes in control rats, pyelonephritic rats, and pyelonephritic rats treated with SkQR1 ($*p<0.05$ vs. control; $**p<0.05$ vs. APN group)
Figure 8E:
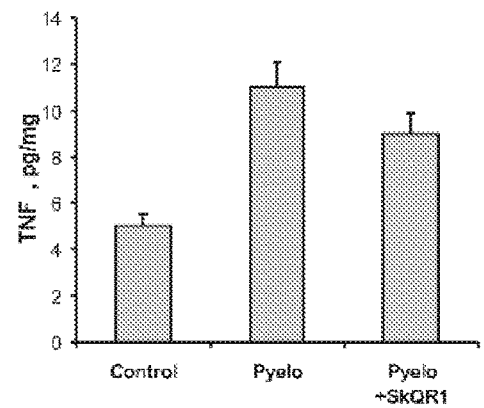
FIG. 8E is a graphic representation of lymphocyte concentration in rats after the induction of pyelonephritis showing the production of pro-inflammatory TNFα.
Figure 8F:
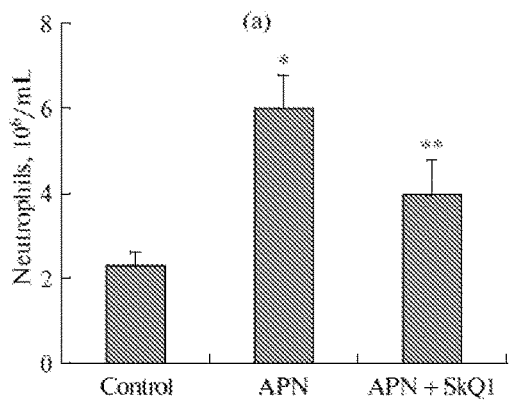
FIG. 8F is a graphic representation of neutrophil concentration in rat blood after the induction of pyelonephritis and treatment with SkQ1.

In the in vivo model of APN, the number of leukocytes in the blood 3 days after infection was increased two fold compared to the control level (FIG. 8A). Pre-treatment with SkQR1 prevented an elevation in the level of leukocytes (FIG. 8A). Leukocytosis correlated with neutrophilia (neutrophil level was three times higher, FIG. 8B). The elevation of the leukocyte concentration was primarily due to the increase in the proportion of neutrophils, since their amount increased almost 5-fold (FIG. 8F). The neutrophil number decreased spontaneously on the 7th day of pyelonephritis in animals in all groups. Monocyte count was also higher in pyelonephritic rats (FIG. 8C) while lymphocyte content in the blood was similar in all three groups (FIG. 8D). On the 3rd day after the induction of pyelonephritis, SkQ1 (100 nmol/kg) was administered intraperitoneally. The effects of APN were inhibited in rats treated with SkQR1 which abolished general leukocytosis and decreased other inflammation markers (FIG. 8A-8C). including a decrease in neutrophils concentration, which on the 7th day was twice as low (FIG. 8F) as that of the animals that did not receive SkQ1. Thus, the treatment with SkQ1 significantly reduced the leukocyte concentration in blood on the 7th day of the disease.

Figure 8G:
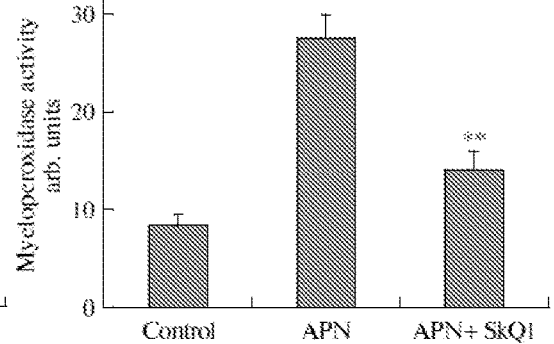
FIG. 8G is a graphic representation of myeloperoxidase (MPO) activity in rats 7 days after the induction of pyelonephritis and treatment with SkQ1.

Furthermore, inflammation in the kidney tissue was also observed. In particular, the activity of MPO, which is a neutrophil enzyme producing hypochlorite in the progression of antibacterial response, increased significantly. MPO is the major enzyme responsible for neutrophil infiltration and for the oxidative burst development in the inflamed tissue as well. On the 7th day of pyelonephritis, its enzymatic activity in the renal tissue was approximately 5 times higher than in the kidney of healthy animals (FIG. 8G)). Intraperitoneal administration of SkQ1 on the third day after pyelonephritis induction resulted in a significant suppression of the inflammation of kidney tissue, as can be concluded from the reduced activity of MPO.

The oxidative-stress-dependent deleterious trend found in kidney tissue under acute pyelonephritis in vivo model was further confirmed in blood leukocytes. Besides a higher level of MDA products in the pyelonephritic kidney tissue (FIG. 5A), leukocytes isolated from rats with APN also had a higher level of ROS. Specifically, flow cytometry analysis demonstrated that the average intensity of DCF fluorescence in the leukocyte population from pyelonephritic rats was about twice as large as in control animals (FIGS. 9A, 9B). In sick animals, leukocytes are in a more activated state. In fact, the addition leukocytic cells from pyelonephritic rats to renal cell cultures caused much more profound oxidative stress in renal cells than that observed under co-cultivation with leukocytes from healthy animals.

Since MTAs demonstrated high potency in preventing oxidative stress in pyelonephritic model in the in vitro model, their effect under APN in rats, an in vivo rat model was studied. ROS production determined by DCF fluorescence measured in leukocytes from pyelonephritic rats receiving SkQR1 was lower than in untreated animals (FIGS. 9A-9D).

Figure 14A:
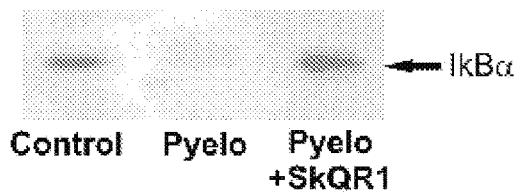
FIG. 14A is a representation of an SDS gel showing activation of NF-κB pathway, as displayed by the expression of IκBα in leukocytes of control rats, pyelonephritic rats, and pyelonephritic rats treated with SkQR1.
Figure 14B:
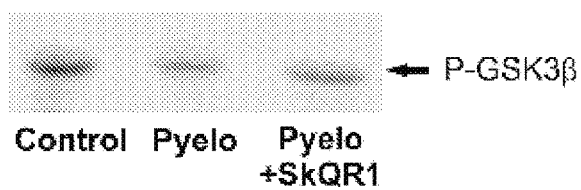
FIG. 14B is a representation of an SDS gel showing the expression of P-GSK3β in leukocytes of control rats, pyelonephritic rats, and pyelonephritic rats treated with SkQR1.
Figure 14C:
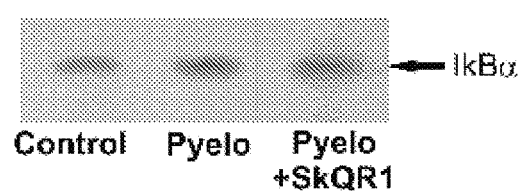
FIG. 14C is a representation of an SDS gel showing IκB content of leukocytes in control rats, pyelonephritic rats, and in pyelonephritic rats treated with SkQR1.
Figure 14D:
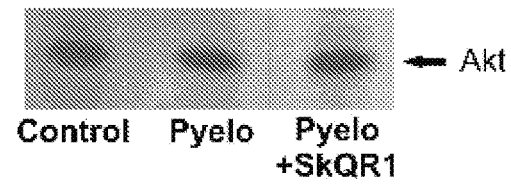
FIG. 14D is a representation showing the concentration of phosphorylated Akt in control rats, pyelonephritic rats, and pyelonephritic rats treated with SkQR1.
Figure 14E:
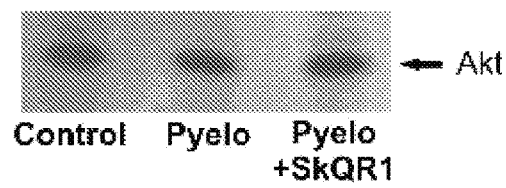
FIG. 14E is a representation of an SDS gel showing the levels of phospho-GSK-3β in control rats, pyelonephritic rats, and pyelonephritic rats treated with SkQR1.

Similarly, pre-treatment with SkQR1 was found to reduce the kidney tissue concentration of TNFα which plays an essential role in inflammatory response (Sanchez-Nino et al. (2010) *Mediators Inflamm.*). Specifically, while in the present model of APN the level of TNFα was twice that of control rats, its level in the kidney tissue of SkQR1-treated pyelonephritic rats was lower than in APN rats without SkQR1 (FIG. 8E). The activation of TNFα production in leukocytes may be mediated by a NF-κB-dependent pathway since the level of IκB in these cells was lower in untreated pyelonephritic rats but not in SkQR1-treated rats (FIG. 14A).

5. Alterations of Anti-Apoptotic Bcl-2 in Pyelonephritic Renal Tissue

3 Cl-2 is an anti-apoptotic (prosurvival) protein found in the mitochondria, and whose levels fall during oxidative stress. The suppression of BCl-2 may induce lower tolerance of the mitochondrial permeability transition to ROS, resulting in a higher rate of cell death.

The balance between apoptotic and anti-apoptotic activities under pyelonephritis was evaluated considering a goal of limiting oxidative stress and its consequences in pyelonephritic kidney tissue, which may be formulated as a development of a cell protective strategy. The level of anti-apoptotic protein Bcl-2 in the tubular cells of the kidney is diminished in the present in vivo model of APN. In the total homogenates of the kidney, a significantly lower Bcl-2 level was observed with the induction of pyelonephritis which was absent in pyelonephritic rats receiving SkQR1 (FIGS. 10A and 10C). Also, the content of Bcl-2 in the mitochondria isolated from kidneys of pyelonephritic animals was 1.5 times lower than in control mitochondria (FIGS. 10A, 10C). In parallel with a weaker band for Bcl-2 at 26 kD, a proportionally stronger band at 15 kD positively stained for Bcl-2 (FIG. 10B, and 10D), suggesting cleavage of Bcl-2 under conditions of pyelonephritis. These changes were diminished after treatment with SkQR1 (FIGS. 10B, 10D).

Thus, pyelonephritis accompanied by oxidative stress causes a significant depression in levels of the anti-apoptotic protein Bcl-2 in mitochondria, the effect being SkQR1-sensitive.

6. The Role of Intercellular Contacts of Leukocytes and Renal Cells

In addition, the morphology of co-cultivated cells was studied by scanning electron microscopy. Renal cells had a morphology typical of epithelial cells, which under the conditions used in this study form semi-monolayer. After 24 hr co-cultivation with a white blood leukocytic fraction, some leukocytic cells (monocytes according to their morphology) were found attached to the renal cells (FIG. 15B). These monocytes appeared to be attached to either cell-free plastic or directly to the renal cell. An earlier study using the same method showed interaction of leukocytes with damaged endothelial cells (Galkina et al. (2004) Med. Sci. Monit. 10:BR307-316). In the present pyelonephritic model, a similar interaction takes place. The fact that TNF release is higher after co-cultivation with renal cells than that observed in a pure culture of activated leukocytes (FIG. 14) suggests the contribution of cell-contact dependent communication between leukocytes and renal cells. Moreover, activated leukocytes died quickly, the death rate being 5-fold lower under conditions of co-culture (FIG. 16).

Experiments with individual leukocytic (LC) and renal cells (RTC) provided additional support for the idea that direct contact of these two kinds of cells is needed to modulate the pro-inflammatory response and cell death. In the next set of experiments, co-cultured cells were separated with a 0.4 µm porous PET membrane (cell culture insert, SPL Lifesciences) which permits communication via exchangeable diffusible compounds but prevents direct contact between the cells. In this system, TNF release is reduced when compared to spatially unrestricted co-culture (Table 1).

TABLE 1

|  | RTC | LC | RTC + LC + bacterial lysate | RTC + LC + bacterial lysate cultivated with separating membrane |
|---|---|---|---|---|
| TNF in the medium, pg/ml | 0 (n = 6) | 2.9 ± 0.8(n = 6) | 16.6 ± 2.9(n = 12) | 5.3 ± 2.2(n = 6) |
| DCF intensity in RTC, arb.units | 1.4 ± 0.1(n = 6) | N/A | 7.4 ± 0.4(n = 12) | 5.1 ± 0.3(n = 6) |

7. Survival of Animals with Acute Pyelonephritis

In the present in vivo model of APN, the mortality of rats was substantial due to development of sepsis (Giamarellos-Bourboulis et al. (2006) Shock 26:410-416). Remarkably, treatment with SkQR1 during first two days after infection resulted in significantly greater animal survival (FIG. 10). This results indicate that mitochondrial ROS production plays a crucial role in APN associated kidney damage and subsequent septic mortality.

Example 2

Effect of SkQ1 on Endothelium Damage

This experiment demonstrates the endothelium damage occurring during inflammatory process and/or diabetes.

High glucose and/or inflammatory cytokines are known to induce endothelial contact disassembly through VE-cadherin cleavage, along with increased oxidative stress and vascular inflammation, leads to endothelial dysfunction and even multiple organ failure.

Human endothelial cell line EA.hy926 (ATCC Collection; catalog number CRL-2922) was used as a model of the endothelium vessel damage occurring during inflammatory process and/or diabetes. This cell line is similar to primary HUVEC cell line (Edgell et al. (1983) PNAS, 80(12):3734-7; Edgell et al. (1990) In Vitro Cell Dev. Biol., 26(12):1167-72) and widely used as a relevant model for inflammation studies (Riesbeck et al. (1998) Clin. Vaccine Immunol., 5:5675-682).

Accordingly, human endothelial cells EA.hy926 were pre-incubated with 2 nM and 20 nM of SkQ1 solution in Dulbecco's Modified Eagle's Medium (DMEM) supplemented with 10% of fetal serum (Example 1) for 4 d. Cells were then incubated 2 d with DMEM medium containing 1% FBS and 5 mM D-glucose. The cells were then incubated 2 d with 45 mM D-glucose and were then used for immunoblotting detection of VE-cadherin.

Figure 17:
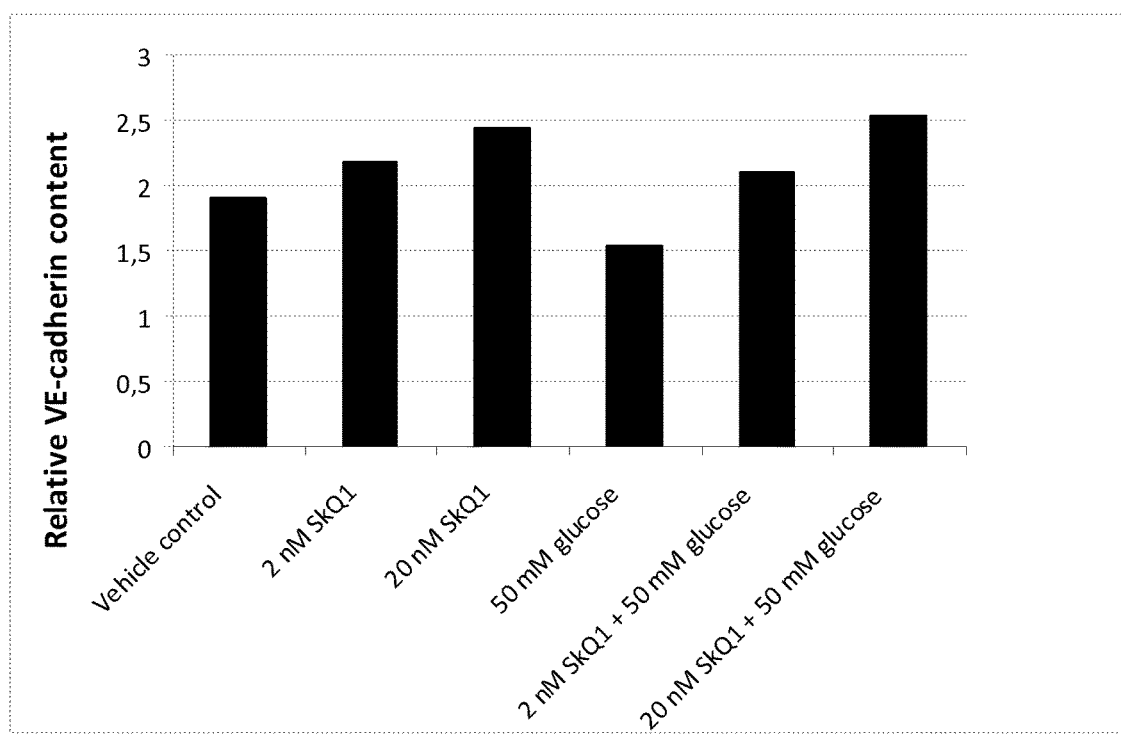
FIG. 17 is a graphic representation demonstrating the anti-inflammatory and anti-diabetic effect of different concentrations of SkQ1 and glucose on endothelial cell contacts as measured by relative VE-cadherin content.

The data from this assay is shown as means at least for 3 separate experiments. As shown in FIG. 17, SkQ1 prevents VE-cadherin downregulation induced by high glucose compared to vehicle control without SkQ1. Thus, SkQ1 was shown to be effective substance protecting endothelial cells against cytokine's inflammatory action, and can be used for prevention and treatment of pathological conditions caused by glucose metabolism disorders including diabetes and hyperglycemia, sepsis, trauma as well as chronicle and acute inflammatory diseases.

Example 3

Effect of SkQ1 on Tissue Damage

Human neutrophils were used as a model of tissue damage occurring during inflammatory processes and/or trauma.

Human neutrophils were isolated from anticoagulated blood of healthy donors. Neutrophils were pre-incubated with 0.2 nM, 2 nM, 20 nM, 200 nM, and 500 nM SkQ1 solution in RPMI-1640 medium supplemented with 10% fetal serum for 1.5 hr at 37° C. in 5% $CO_2$. The cells were then stimulated with 1 nM N-formyl-methionine-leucine-phenylalanine (f-MLP) for 30 min. The supernatants from the cells were used to detect MMP-9 activity by zymography analysis (MMP-9 release was used to estimate tissue damage). The data from this assay was shown as means at least for 3 separate experiments.

Figure 18:
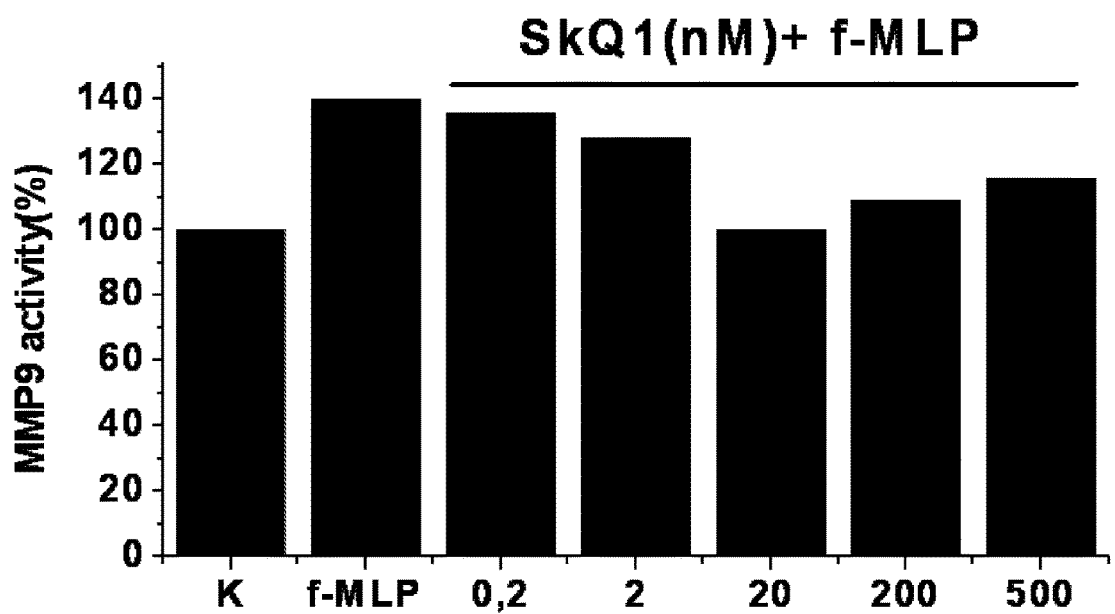
FIG. 18 is a graphic representation demonstrating the anti-inflammatory effect of different concentrations of SkQ1 and f-MLP on human neutrophils (gelatinase activity as measured by MMP9 activity)

As shown in FIG. 18, SkQ1 at concentrations of 0.2 nM, 2 nM, and 200 nM prevented neutrophil-MMP-9 activation induced by f-MLP, compared to the vehicle control without SkQ1.

Thus, because SkQ1 is effective in protecting human tissues against damage caused by pathogens and/or inflammatory cytokines, it is thus useful for prevention and treatment of bronchial asthma, chronic obstructive pulmonary disease, ischemia, acute aortic dissection, kidney disease, trauma, sepsis, and other inflammatory diseases.

Example 4

Protective Effect of MTAs in a Hepatitis Model

Experimental hepatitis was induced in 8-10 weeks old Wistar rats weighing 80 g-120 g by intraperitoneal injection of 500 mg/kg D-galactosamin in 0.9% NaCl. SkQ1 was administered by gavage in aqueous solution at doses of 10 nmol/kg/day, 50 nmol/kg/day, 250 nmol/kg/day, and 1250 nmol/kg/day starting 7 d before induction of hepatitis and ending at the day of induction. The animals were sacrificed 24 hrs after the induction of hepatitis. Inflammation score was estimated for each animal on a 3-point scale by blind examination of hematoxylin-eosin stained liver sections.

Figure 19:
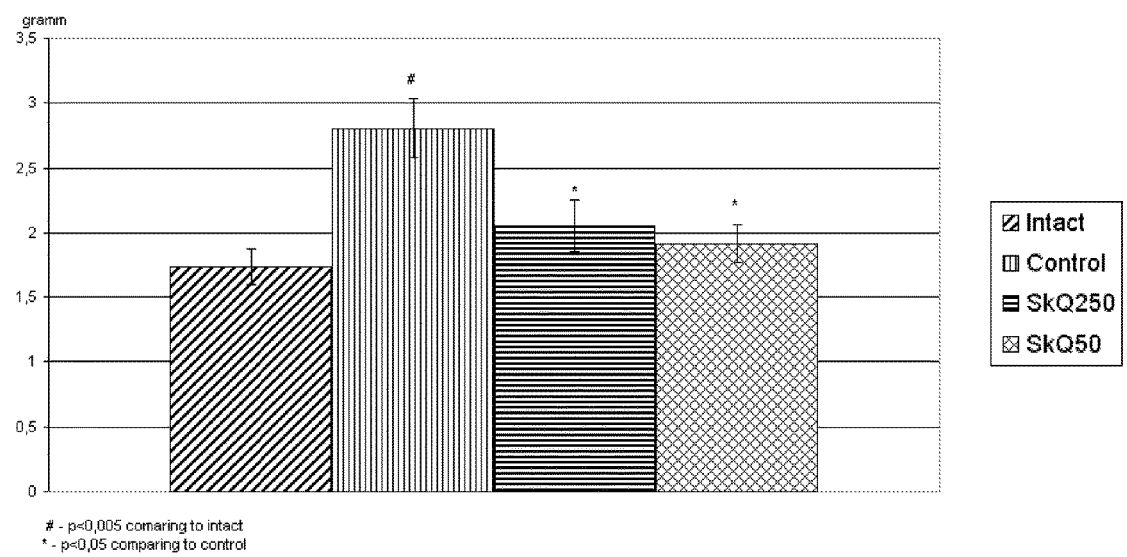
FIG. 19 is a graphic representation showing SkQ1 that treatment prevents pancreatic edema in the model of acute pancreatitis, where the weight in grams of the pancreas of 4 groups of animals is shown (average and SE are indicated).

As shown in FIG. 19, SkQ1 at 1250 nmol/kg/day reduced the inflammation score from median of 2 in the control group to median of 1 (p<0.001). SkQ1 at 50 nmol/kg/day reduced the inflammation score to 1.5 (p<0.01).

Example 5

Protective Effect of MTAs in a Pancreatitis Model

42 Wistar rats (age: 20-25 week, weight 400 g-750 g) were distributed among 4 experiemntal groups with the same average weight. SkQ1 was administered with drinking water with an estimated dosage of 250 nmoles/kg/day or 50 nmoles/kg/day. Acute pancreatitis was induced by a single intraperitoneal (ip) injection of arginine (100 mg/100 g of animal weight; 20% arginine solution in about 2.5 ml phosphate buffer).

The experimental groups were: (1) Intact (n=10); (2) Control (n=10) treated with arginine ip injection; (3) SkQ250-SkQ1 pretreatment with 250 nmoles/kg/day dosage for 9 days; IP injection of arginine on day 9, continuation of SkQ1 treatment for 24 hr (n=10); and (4) SkQ50-SkQ1 pretreatment with 50 nmoles/kg/day dosage for 9 days. IP injection of arginine on day 9, continuation of SkQ1 treatment for 24 hr (n=10).

The results shown in FIG. 19 demonstrate that both dosages of SkQ1 prevented an increase in the weight of the pancreas, thus dramatically reducing the edema caused by inflammation.

The activity of pancreatic myeloperoxidase (MPO) was also measured as described in Example 1 (for kidney tissue).

The results show that SkQ1 treatment was shown to significantly reduce MPO activity, and thus, inflammation in pancreatic tissue homogenates (Table 2).

TABLE 2

| Experimental group | MPO activity | Standard Error |
|---|---|---|
| Intact | 6.1 | 2.5 |
| Control | 52.9 | 9.9 |
| SkQ250 | 15.8 | 3.2 (p = 0.005 comparing to control group) |
| SkQ50 | 50.0 | 13.7 |

Histopathological examination of the rat pancreas samples also revealed the beneficial effect of SkQ1. Samples of pancreas were fixed in 10% formalin and then prepared for eosin-hematoxylin staining of 5 μm-6 μm slices using standard techniques. Stained samples (slices) were examined under light microscopy.

The intensity of inflammation in the samples was measured by a standard ascending scale score from 0 to 3. The average score of inflammation in rats without SkQ treatment was 1.5. SkQ1 in a dosage of 250 nmol/kg/day significantly decreased the inflammation average score to 0.6 (p<0.01; Mann-Whitney test). The results are shown in Table 3.

TABLE 3

| Experimental Group | Average inflammation score |
|---|---|
| Control without pancreatitis (n = 7) | 0 |
| Untreated pancreatitis (n = 12) | 1.5 |
| SkQ50 (n = 11) | 1.5 |
| SkQ250 (n = 9) | 0.6 (p < 0.01) |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A method of treatment of an inflammatory disorder selected from the group consisting of acute pyelonephritis, hepatitis, and pancreatitis, the method comprising treating a subject having the inflammatory disorder with one or more mitochondrially targeted antioxidant having the structure:

wherein:
A is an effector moiety having a following structure:

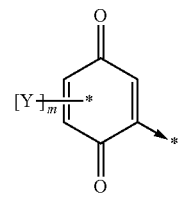

and reduced forms thereof, wherein:
m is an integer from 1 to 3;
each Y is independently selected from the group consisting of:
lower alkyl;
lower alkoxy; or
two adjacent Y groups, together with carbon atoms to which they are attached, form a following structure:

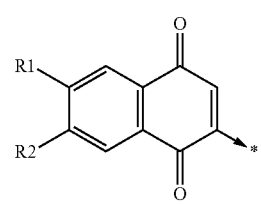

and reduced forms thereof; wherein:
R1 and R2 may be the same or different and are each independently lower alkyl or lower alkoxy;
L is a linker group, comprising:
a) a straight or branched hydrocarbon chain which can be optionally substituted by one or more substituents and optionally contains one or more double or triple bonds; or
b) a natural isoprene chain;
n is integer from 1 to 40, or from 2 to 15, or from 5 to 11;
B is a targeting group comprising Sk$^+$Z$^-$, wherein:
Sk is a lipophilic cation; and
Z is a pharmacologically-acceptable anion;
and solvates, salts, and stereoisomers thereof.

2. The method of claim 1, wherein the antioxidant is one or more of SkQ1:

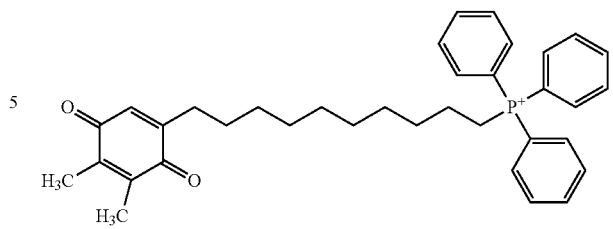

and its reduced (quinole) form SkQ1H$_2$.

3. The method of claim 1, wherein the antioxidant is one or more of SkQR1:

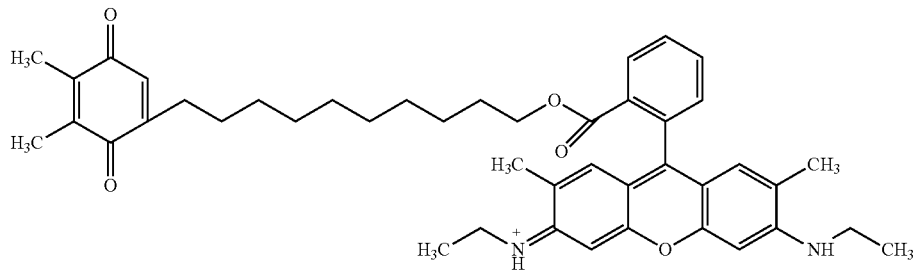

SkQR1 and its reduced (quinole) form SkQR1H$_2$.

4. The method of claim 1, wherein the antioxidant is one or more of SkQ3:

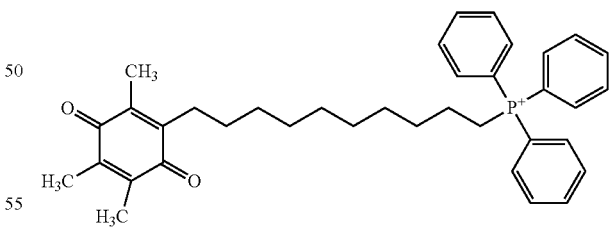

SkQ3 and its reduced (quinole) form SkQ3H$_2$.

5. The method of claim 1, wherein the antioxidant is one or more of SkQRB:

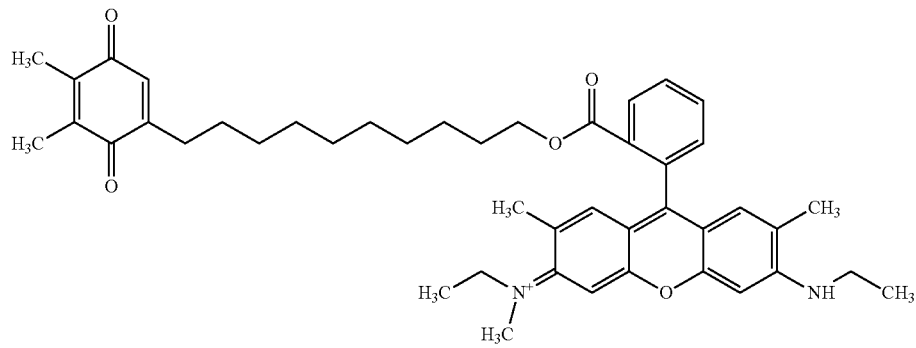 [SMILES: CCNc1cc2oc3c/c(=[N+](\C)CC)c(C)cc-3c(-c3ccccc3C(=O)OCCCCCCCCCCC3=CC(=O)C(C)=C(C)C3=O)c2cc1C]

and its reduced (quinole) form SkQRBH$_2$.

6. The method of claim 1, wherein the antioxidant is one or more of SkQB1:

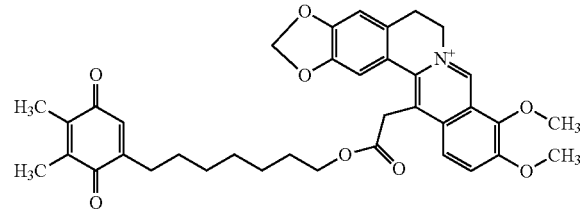

and its reduced (quinole) form, SkQB1H$_2$.

7. The method of claim 1, wherein the antioxidant is one or more of SkQBP1:

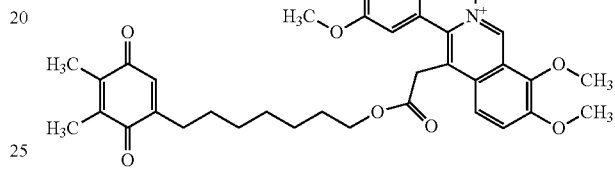

and its reduced (quinole) form SkQBP1H$_2$.

8. The method of claim 1, wherein the antioxidant is one or more of SkQ1, SkQ1H$_2$, SkQR1, SkQR1H$_2$, SkQ3, SkQ3H$_2$, SkQRB, SkQRBH$_2$, SkQB1, SkQBH$_2$, SkQBP1, and SkQBP1H$_2$.

* * * * *